United States Patent [19]

Vorbrüggen et al.

[11] 4,217,360
[45] Aug. 12, 1980

[54] NOVEL 1,3-BENZODIOXANEPROSTANOIC ACID DERIVATIVES AND PROCESS FOR THE PREPARATION THEREOF

[75] Inventors: Helmut Vorbrüggen; Norbert Schwarz; Olaf Loge; Walter Elger, all of Berlin, Fed. Rep. of Germany

[73] Assignee: Schering Aktiengesellschaft, Berlin & Bergkamen, Fed. Rep. of Germany

[21] Appl. No.: 2,268

[22] Filed: Jan. 10, 1979

Related U.S. Application Data

[63] Continuation of Ser. No. 888,059, Mar. 20, 1978, abandoned, which is a continuation of Ser. No. 800,126, May 24, 1977, abandoned, which is a continuation of Ser. No. 659,130, Feb. 18, 1976, abandoned.

[30] Foreign Application Priority Data

Feb. 27, 1975 [DE] Fed. Rep. of Germany ....... 2508826

[51] Int. Cl.² ........................................... C07D 319/08
[52] U.S. Cl. ................................ 424/278; 260/340.3; 542/426; 542/429; 542/430
[58] Field of Search ..................... 542/429, 426, 430; 260/340.3, 340.7; 424/278

[56] References Cited

U.S. PATENT DOCUMENTS

| | | | |
|---|---|---|---|
| 3,956,284 | 5/1976 | Hess et al. | 542/429 |
| 3,962,218 | 6/1976 | Raduchel et al. | 542/429 |
| 4,000,311 | 12/1976 | Gätzi et al. | 424/278 |
| 4,004,020 | 1/1977 | Skuballa | 542/429 |
| 4,004,021 | 1/1977 | Bowler et al. | 542/429 |
| 4,011,242 | 3/1977 | Libit | 260/340.3 |

Primary Examiner—Arthur P. Demers
Attorney, Agent, or Firm—Millen & White

[57] ABSTRACT 1,3-Benzodioxaneprostanoic acid compound of the formula

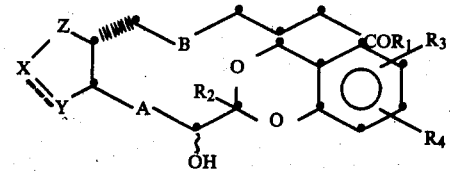

wherein $R_1$ is hydroxy, alkoxy of 1-10 carbon atoms, methylsulfamido, substituted or unsubstituted aryloxy, or $O-CH_2-U-V$ wherein U is a direct bond, carbonyl, or carbonyloxy, and V is phenyl or phenyl substituted, e.g. by one or more of phenyl, phenoxy, alkoxy of 1-2 carbon atoms, and halogen; A is $-CH_2-CH_2-$ or trans $-CH=CH-$; B is $-CH_2-CH_2-$ or cis- or trans$-CH=CH-$; Z is hydroxymethylene or carbonyl; X------Y, if Z is hydroxymethylene, is

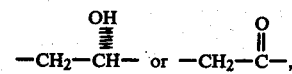

or, if Z is carbonyl, is

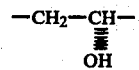

or $-CH=CH-$; $R_2$ is hydrogen or alkyl of 1-5 carbon atoms; $R_3$ and $R_4$ each are H, F, Cl, Br, I or $CF_3$, $CH_3$ or alkoxy of 1-2 carbon atoms or $R_3$ and $R_4$ in 6-,7-position is methylendioxy; and if $R_1$ is hydroxy, salts thereof with pharmaceutically acceptable bases, are agents for inducing menstruation, interrupting pregnancy, inducing labor and synchronizing the sexual cycle in female mammals.

76 Claims, No Drawings

NOVEL 1,3-BENZODIOXANEPROSTANOIC ACID DERIVATIVES AND PROCESS FOR THE PREPARATION THEREOF

This is a continuation or application Ser. No. 888,059, filed on Mar. 20, 1978, now abandoned, which is a continuation of Ser. No. 800,126, filed on May 24, 1977, now abandoned, which in turn is a continuation of Ser. No. 659,130, filed on Feb. 18, 1976, now abandoned.

BACKGROUND OF THE INVENTION

The various effects of prostaglandins in mammalian organisms, as well as in vitro, are of brief duration, since the prostaglandins are rapidly converted to pharmacologically inactive metabolic products. For example, an inactive metabolite is formed by oxidation of the allylic hydroxy function at the 15 carbon atom by 15-hydroxyprostaglandin dehydrogenases.

Therefore, the need to develop prostaglandin analogs which have a spectrum of activity comparable to that of natural prostaglandins, but longer duration and selectivity of activity, has been apparent.

1,3-Benzodioxaneprostaglandins surprisingly show a longer duration of activity, a higher selectivity and a higher effectiveness than naturally occurring protaglandins.

SUMMARY OF THE INVENTION

In a compositional aspect, this invention relates to 1,3-benzodioxaneprostanoic acid compounds of Formula I

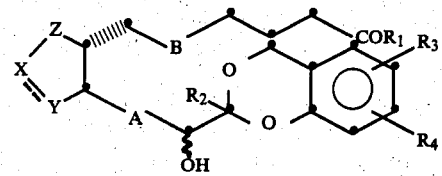

wherein $R_1$ is hydroxy; alkoxy of 1–10 carbon atoms; methylsulfamido; substituted or unsubstituted aryloxy; or $O-CH_2-U-V$, wherein U is a direct bond, carbonyl, or carbonyloxy, and V is phenyl or phenyl substituted, e.g. by one or more phenyl, phenox alkoxy of 1–2 carbon atoms or halogen. A is $-CH_2-CH_2-$ or trans$-CH=CH-$; B is $-CH_2-CH_2-$ or cis- or trans$-CH=CH-$; Z is hydroxymethylene or carbonyl. X $=\!=\!=\!=\!$ Y, when Z is hydroxymethylene, is

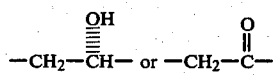

or, when Z is carbonyl, is

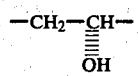

or $-CH=CH-$; $R_2$ is hydrogen or alkyl of 1–5 carbon atoms; $R_3$ and $R_4$ are alike or different and each is H, F, Cl, Br, I, $CF_3$, $CH_3$, or alkoxy of 1–2 carbon atoms or $R_3$ and $R_4$ in 6-,7-position is methylenedioxy; and when $R_1$ is hydroxy, salts thereof with pharmaceutically acceptable bases, including both the optical antipodes and racemates thereof.

In another compositional aspect, this invention relates to novel lactol intermediates of Formula II hereinafter.

In another compositional aspect, this invention relates to a pharmaceutical composition for inducing menstruation, interrupting pregnancy, inducing labor or synchronizing the sexual cycle in female mammals, comprising a compound of Formula I or a salt thereof with a pharmaceutically acceptable carrier, in admixture with a pharmaceutically acceptable carrier In another aspect, this invention relates to methods of using a compound of Formula I or a salt thereof with a pharmaceutically acceptable carrier for interrupting pregnancy or inducing labor in a pregnant female mammal or synchronizing the sexual cycle of a sexually mature female mammal.

In another aspect, this invention relates to a process for preparing 1,3-benzodiaxaneprostanoic acids of Formula I, comprising reacting a lactol of Formula II

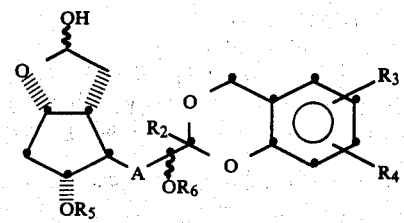

wherein $R_2$, $R_3$, $R_4$, and A are as above and $R_5$ and $R_6$ each are hydrogen or a hydroxy blocking group, with a Wittig reagent of Formula III

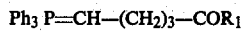

wherein Ph is phenyl and $R_1$ is as above;

and, optionally after oxidation of the 9-hydroxy group cleaving of any remaining hydroxy blocking groups;

and, in any desired sequence, esterifying a free 1-carboxy; saponifying an esterified 1-carboxy group; and/or reducing a 9-keto group and/or hydrogenating a 5,6-double bond; and/or hydrogenating a 13,14- and 5,6-double bond; and/or dehydrating a 9-keto compound and eliminating an 11-hydroxy; and or blocking the 11- and 15-hydroxy and oxidizing the 9-hydroxy; and/or blocking the 9- and 15-hydroxy groups and oxidizing the 11-hydroxy; and converting a 1-carboxy compound with a base to a pharmaceutically acceptable salt and/or separating the reacemates thereof.

DETAILED DESCRIPTION

Substituted or unsubstituted $R_1$ aryloxy groups include phenoxy, 1-naphthoxy and 2-naphthoxy, each of which can be mono-, di- or poly-substituted, e.g., by 1–3 halogen atoms, phenyl, phenoxy, 1–3 alkyl or alkoxy of 1–4 carbon atoms, one each of chloromethyl, fluoromethyl, trifluoromethyl, carboxy and hydroxy. Preferred are chloro, bromo, trifluoromethyl, phenyl, phenoxy, methoxy.

$R_1$ alkoxy groups include straight- and branched-chain, saturated and unsaturated alkoxy of 1–10 carbon atoms. Saturated alkoxy of 1–6 carbon atoms are preferred. Examples of $R_1$ alkoxy include methoxy, ethoxy, propoxy, butoxy, isobutoxy, tert.-butoxy pentoxy, hexoxy, heptoxy, octoxy, butenyloxy, isobutenyloxy, propenyloxy.

$R_1$ can also be methylsulfamido, i.e., $CH_3SO_2NH-$, or $-O-CH_2-U-V$, i.e., $-O-CH_2-V$, $-O-CH_2CO-V$ and $-O-CH_2COO-V$ wherein V is, e.g., p-Cl-phenyl, p-F-phenyl, p-Br-phenyl, phenyl, m-methoxyphenyl, p-phenylphenyl, p-phenoxyphenyl.

Examples of $R_2$ alkyl groups of 1–5 carbon atoms are methyl, ethyl, propyl, isopropyl, butyl, isobutyl, and pentyl.

Any inorganic or organic base known to those skilled in the art for the production of physiologically compatible salts can be employed. Examples are alkali metal hydroxides, such as sodium or potassium hydroxide; alkaline earth hydroxides, such as calcium hydroxide; ammonia; amines, such as ethanolamine, diethanolamine, triethanolamine, N-methylglucamine, morpholine, and tris(hydroxymethyl)-methylamine, etc.

Compounds of Formula I which are preferred incorporate one or more of the preferred functions of $R_1$, A, B, Z, X=====Y, $R_2$, $R_3$ or $R_4$, include the following compounds, which otherwise correspond to Formula I, but wherein:

(a) A is $-CH_2CH_2-$;
(b) A is trans- $-CH=CH-$;
(c) B is $-CH_2CH_2-$, including each of (a)–(b);
(d) B is cis- $-CH=CH-$, including each of (a)–(b);
(e) B is trans- $-CH=CH-$, including each of (a)–(b);
(f) Z is hydroxymethylene and X=====Y is

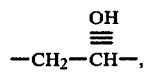

including each of (a)–(e);
(g) Z is hydroxymethylene and X=====Y is

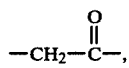

including each of (a)–(e);
(h) Z is carbonyl and X=====Y is

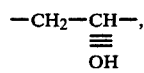

including each of (a)–(e);
(i) Z is carbonyl and X=====Y is $-CH=CH-$, including each of (a)–(e);
(j) $R_1$ is hydroxy, including each of (a)–(i);
(k) $R_1$ is alkoxy of 1–10 carbon atoms, including each of (a)–(i);
(l) $R_1$ is methoxy and $R_3$ and $R_4$ are H, including each of (a)–(i); and
(m) $R_1$ is p-phenylphenacyloxy and $R_3$ and $R_4$ are H, including each of (a)–(i).

Reaction of lactols II with a Wittig reagent of Formula III, produced from the corresponding phosphonium bromide and methanesulfinylmethylsodium or potassium tert.-butylate in the usual way in dimethyl sulfoxide, is accomplished at temperatures of 0°–100° C., preferably at 20°–80° C., in an aprotic solvent, preferably dimethyl sulfoxide or dimethylformamide. The Wittig reagent can also be liberated by reaction of 4—$R_1$—CO—triphenylbutylphosphonium bromide with potassium tert.-butylate.

Oxidation of the 9-hydroxy group to the ketone, which can take place before splitting off the hydroxy blocking groups, is effected with the customary oxidizing agents, e.g., with Jones reagent (J. Chem. Soc. 1953, 2555). The reaction is conducted in an excess of the oxidizing agent in a suitable diluent, such as acetone, at temperatures of between 0° C., and −50° C., preferably at −20° C. The reaction is generally finished after 5–30 minutes.

The oxidation of the 9-hydroxy group takes place preferably after first blocking the 11- and 15-hydroxy groups, e.g., by silylation (Chem. Comm. [1972], 1120). Other usable oxidizing agents are silver carbonate on "Celite" or mixtures of chromium trioxide and pyridine (Tetrahedron Letters 1968, 3363).

The 11-hydroxy group is oxidized by the usual oxidizing agents, e.g, with Jones reagent or Collins reagent, after first blocking the 9- and 15-hydroxy groups. This reaction is carried out at temperatures of between −40° C. and +20° C., preferably at −20° C.

Suitable hydroxy blocking groups $R_5$ and $R_6$ are known to those skilled in the art, preferably cyclic $\alpha,\beta$-unsaturated ethers, for example, dihydropyran, dihydrofuran, and $\alpha$-ethoxyethylene; and acyl residues, e.g., aromatic and aliphatic organic acid groups, preferably benzoyl and acetyl.

OH blocking groups, e.g., THP and THF ethers, are removed to obtain compounds of Formula I by conventional methods in an aqueous solution of an organic acid, for example, acetic acid, propionic acid, etc., or in an aqueous solution of an inorganic acid, e.g., hydrochloric acid. To improve solubility, a water-miscible inert organic solvent is advantageously added. Suitable organic solvents are alcohols, such as methanol and ethanol, and ethers, such as dimethoxyethane, dioxane, and tetrahydrofuran. Tetrahydrofuran is preferably employed. The hydrolysis is executed preferably at temperatures of between 20° C. and 80° C. In case of compounds of the prostaglandin E type, the hydrolysis is conducted at below 45° C. to avoid the formation of prostaglandin A compounds as by-products.

The acyl groups are split off with alkali metal carbonates, e.g., potassium carbonate in methanol at 0°–50° C., preferably at 25° C.

Reduction of the 9-oxo group to obtain a mixture of epimeric 9-$\alpha$- and 9-$\beta$-alcohols is conducted in the usual way, preferably in an organic solvent with sodium borohydride or zinc borohydride. If zinc borohydride is used, suitable solvents include dimethoxyethane, diethyl ether, dioxane, benzene and isopropyl ether. When using sodium borohydride, solvents which can be used are methanol, ethanol, isopropanol and n-propanol. The thus-formed mixture of epimers is separated by column or layer chromatography and/or fractional crystallization.

Dehydration of the 9-oxo compound, wherein the 11-hydroxy group and a hydrogen atom for the 10-position are split off, to form a prostaglandin A derivative can be conducted under conditions generally known to a person skilled in the art. In general, the dehydration is effected in a solution of an organic acid, such as acetic acid, or an inorganic acid, such as hydrochloric acid, at temperatures of between 20° C. and 80° C. The reaction is terminated after about 2 to 17 hours.

The hydrogenation of the 13,14- and/or 5,6-double bond is accomplished in a hydrogen atmosphere and in the presence of a noble metal catalyst. A suitable catalyst is, for instance, 10% palladium on charcoal. If the hydrogenation is conducted at room temperature, the 5,6- and 13,14-double bonds can be saturated. At low temperatures, preferably at −80° C. to −10° C., the cis-5,6-double bond can be hydrogenated before the trans-13,14-double bond. Selective reduction of the cis-5,6-double bond in a compound with a trans-13,14-double bond is also effected using nickel boride or tris(triphenylphosphine)rhodium(I) chloride as catalyst.

In order to prepare the esters of Formula I wherein $R_1$ is alkoxy of 1-10 carbon atoms, the 1-carboxy compounds are reacted conventionally with diazohydrocarbons. The esterification with diazo-hydrocarbons takes place by mixing a solution of the diazo-hydrocarbon in an inert solvent, preferably in diethyl ether, with the 1-carboxy compound in the same inert solvent or in another inert solvent, e.g., methylene chloride. After the reaction is finished (within 1-30 minutes), the solvent is removed and the ester purified in the usual manner.

Diazoalkanes are either known or can be prepared in accordance with conventional methods. Org. Reactions 8: 389–394 (1954).

To introduce the ester group O—CH₂—U—V— for $R_1$, a 1-carboxy compound of Formula I is reacted, in the presence of a hydrogen halide acceptor, with a halogen compound of the formula

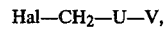

wherein Hal is halogen, preferably bromine; U is a direct bond, a carbonyl or carbonyloxy, and V is phenyl or phenyl substituted e.g. by one ore more phenyl, phenoxy, alkoxy of 1-2 carbon atoms or halogen, preferably bromine.

Suitable hydrogen halide acceptors include silver oxide, sodium carbonate, potassium carbonate, sodium bicarbonate, potassium bicarbonate, or amines, such as trimethylamine, triethyamine, tributylamine, trioctylamine, and pyridine. The reaction with the halogen compound is accomplished in an inert solvent, preferably in acetone, acetonitrile, dimethylacetamide, dimethylformamide, or dimethyl sulfoxide at temperatures of −80° C. to +100° C., preferably at room temperature.

In order to prepare esters of Formula I wherein $R_1$ is a substituted or unsubstituted aryloxy group, the 1-carboxy compounds are reacted with the corresponding arylhydroxy compounds and dicyclohexylcarbodiimide in the presence of a suitable base, e.g., pyridine or triethylamine, in an inert solvent. Suitable solvents are methylene chloride, ethylene chloride, chloroform, ethyl acetate, tetrahydrofuran, preferably chloroform. The reaction is conducted at temperatures of between −30° C. and +50° C., preferably at 10° C.

The saponification of the prostaglandin esters takes place according to the methods known to those skilled in the art, for example, with potassium hydroxide in methanol.

The prostaglandin derivatives of Formula I wherein $R_1$ is hydroxy can be converted into salts by neutralization with equivalent amounts of the corresponding inorganic bases. For example, the corresponding PG acid is dissolved in water containing the stoichiometric quantity of the base. The solid inorganic salt is obtained after evaporation of the water and after adding a water-miscible solvent, e.g., alcohol or acetone.

To produce an amine salt, the PG acid is dissolved in a suitable solvent, e.g., ethanol, acetone, diethyl ether, or benzene, and at least a stoichiometric amount of the amine is added to the solution. The salt is ordinarily obtained as a solid.

The lactols of Formula II serving as the starting compounds can be produced by reacting 2-hydroxy-methylphenols (saligenins) with dihalocarboxylic acids to give 1,3-benzodioxane 2-carboxylic acids of Formula IV

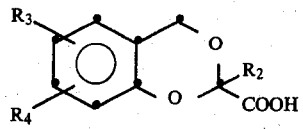

The thus-obtained 1,3-benzodioxane-2-carboxylic acid is present as the racemate because of the asymmetrical carbon atom in the 2-position. The racemate can be separated by salt formation with optically active bases into the optical antipodes. The subsequent esterification can be conducted with the racemate and/or with the enantiomer. The thus-obtained 1,3-benzodioxane-2-carboxylic acid ester is reacted with triphenylphosphine methylene or a methylphosphonic acid dialkyl ester. From the product, a ketone of Formula V below is then prepared in a conventional manner by a Wittig and/or a Wittig-Horner reaction with an aldehyde (preferably in the form of the corresponding antipode)

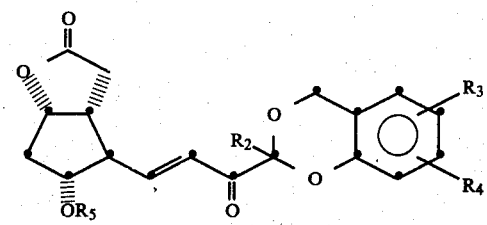

The $C_{16}$-diastereomer mixture which may thus have been produced can be separated according to the usual methods.

In the presence of noble metal salt catalysts, the keto of general Formula V can be hydrogenated, if desired, in the 13,14-position (PG numbering) in an inert solvent.

The subsequently conducted reduction to the α- and β-$C_{15}$-alcohols takes place with sodium borohydride or zinc borohydride. The mixture of epimers can be separated according to the customarily known methods. After the introduction of hydroxy blocking groups, such as, for example, dihydropyran, in position 15 and optionally in position 11 (PG numbering), the lactone is reduced to the desired lactol of general Formula II with diisobutylaluminum hydride and/or lithim tri-tert.-butoxyaluminum hydride.

The reduction to the lactol of general Formula II can also be conducted without blocking groups according to a simplified Corey synthesis as described in DOS (German Unexamined Laid-Open Application) 2,328,131 with diisobutylaluminum hydride or lithium tri-tert.-butoxyaluminum hydride.

To introduce the hydroxy blocking groups, the 11,15-diol (PG numbering) is reacted with, for example, dihydropyran in methylene chloride or chloroform with the use of an acidic condensation agent, e.g. p-toluenesulfonic acid. The dihydropyran is used in an excess, preferably 4 to 10 times the theoretical quantity. The reaction is normally terminated after 15-30 minutes when conducted at 0° C.-30° C.

One possibility for producing the starting compounds acetylated in the 11-position is to react the lactol, etherified in the 15-position (PG numbering), with acetic anhydride in pyridine. After liberating the lactolhydroxy group, a lactol of general Formula II is obtained.

The novel prostanoic acid derivatives of general Formula I are valuable pharmaceutical agents, since they show, with a similar spectrum of activity, a substantially stronger and, in particular, longer lasting effect than the corresponding natural prostaglandins.

The novel prostaglandin analogs of the E, D, and F type have a very strong luteolytic effect, i.e., for triggering luteolysis, at lower doses than the corresponding natural prostaglandins.

When recording the isotonic uterus contraction on narcotized rats and on the isolated rat uterus, it is found that the compounds of this invention are substantially more effective and their activities are of a longer duration than in case of the natural prostaglandins, as demonstrated by the following table, using compounds 1–8 of this invention as examples, in comparison to the natural PG $F_{2\alpha}$. The investigations were carried out on gravid rats according to the usual methods. Thus, gravid rats were treated, subcutaneously with the compounds of this invention. On the ninth day, the animals were sacrificed and the uteri examined for points of implantation.

TABLE

| | Compound Investigated | Relative Effect PG F $_{2\alpha}$ = 1 on Abortion in Rats |
|---|---|---|
| 1 | Methyl ester of (5Z,13E)-(8R,9S,11R,12R,15R)-9,11,15-trihydroxy-15-({2S}-1,3-benzodioxan-2-yl)-16,17,18,19,20-pentanor-prostadienoic acid | 300 |
| 2 | Methyl ester of (5Z,13E)-(8R,9S,11R,12R,15R)-9,11,15-trihydroxy-15-({2RS}-1,3-benzodioxan-2-yl)-16,17,18,19,20-pentanor-prostadienoic acid | 30 |
| 3 | (4-Phenyl)-phenacyl ester of (5Z,13E)-(8R,9S,11R,12R,15R)-9,11,15-trihydroxy-15-({2S}-1,3-benzodioxan-2-yl)-16,17,18,19,20-pentanor-prostadienoic acid | 30 |
| 4 | (4-Phenyl)-phenacyl ester of (5Z,13E)-(8R,9S,11R,12R,15S)-9,11,15-trihydroxy-15-({2S}-1,3-benzodioxan-2-yl)-16,17,18,19,20-pentanor-prostadienoic acid | 3 |
| 5 | (5Z,13E)-(8R,9S,11R,12R,15R)-9,11,15-Trihydroxy-15-({2R}-1,3-benzodioxan-2-yl)-16,17,18,19,20-pentanor-prostadienoic acid | 3 |
| 6 | Methyl ester of (5Z,13E)-(8R,9S,11R,12R,15R)-9,11,15-trihydroxy-15-({2R}-1,3-benzodioxan-2-yl)-16,17,18,19,20-pentanor-prostadienoic acid | 3 |
| 7 | Methyl ester of (5Z,13E)-(8R,9S,11R,12R,15S)-9,11,15-trihydroxy-15-({2RS}-1,3-benzodioxan-2-yl)-16,17,18,19,20-pentanor-prostadienoic acid | 10 |
| 8 | Methyl ester of (5Z,13E)-8R,9S,11R,12R,15S)-9,11,15-trihydroxy-15-({2R}-1,3-benzodioxan-2-yl)-16,17,18,19,20-pentanor-prostadienoic acid | 10 |

As demonstrated by the table, the compounds of this invention are of the same abortive effectiveness in doses which are 3 to 300 times lower per 1 mg. per animal than PG $F_{2\alpha}$.

The novel prostanoic acid derivatives are suitable, by one-time intrauterine application, for inducing menstruation or interrupting a pregnancy. They are furthermore suitable for snychronizing the sexual cycle in female mammals, such as cattle, monkeys, pigs, rabbits, etc.

The high dissociation of effectiveness of the compound according to the present invention manifests itself in their effect on other smooth-muscle organs, for example, on the guinea pig ileum or on the isolated rabbit trachea, where substantially lesser stimulation is observed than with natural prostaglandins.

Active agents of the PG E series according to the invention show in vitro, on the isolated rabbit trachea, a broncho-dilatory effect and greatly inhibit stomach acid secretion. The also have a regulating effect on cardiac dysrhythmias. The novel compounds of the PG A and PG E series additionally lower blood pressure and have a diuretic effect.

Active agents of the F series have a lower bronchoconstrictive effect than natural prostaglandin $F_{2\alpha}$, which is of great advantage for their therapeutic application.

For medical use, the active agents can be converted into a form suitable for inhalation or for oral or parenteral application.

For inhalation purposes, aerosol or spray solutions are advantageously prepared.

Suitable for oral application are, for example, tablets, dragees, or capsules.

For parenteral administration, sterile, aqueous or oily solutions which can be injected are utilized.

The invention also relates to medicinal agents comprise compounds of Formula I and customary auxiliary agents and carriers. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic wetting agents, buffers, or salts for influencing osmotic pressure, etc. Sprayable aerosol preparations of compounds of Formula I, preferably in combination with a solid or liquid inert carrier material, are packaged in a squeeze bottle or in admixture with a pressurized volatile, normally gaseous propellant, e.g., a freon.

The active agents of this invention are useful, in conjunction with the auxiliary substances known and customary in galenic pharmacy, in preparations for triggering abortion, for menstrual cycle control, or for the induction of labor. For the latter purpose, sterile, aqueous solutions can be employed containing 0.01–10 μg./ml. of the active ingredient and used in the form of an intravenous infusion solution. To produce aqueous, isotonic solutions, acids and salts of Formula I are especially suitable. Alcohols, such as ethanol and propylene glycol, can be added to increase solubility.

In addition to the compounds of the Examples hereinafter, illustrative embodiments of the compounds of Formula I are: Methylsulfamid of (13E)-(8R,11R,12R,15R)-9-oxo-11,15-dihydroxy-15-({2RS}-1,3-benzodioxan-7-trifluoromethyl-2-yl)-16,17,18,19,20-pentanor-13-prostemoic acid (4-phenyl)-phenacyl ester of (5Z)-(8R,9S,11R,12R,15S)-9,11,15-Trihydroxy-({2RS}-1,3-benzodioxan-8-methoxy-2-yl)-16,17,18,19,20-pentanor-5-prostenoic acid (4-bromo)-phenacyl ester of (5Z,13E)-(8R,11R,12R,15R)-9-oxo-11,15-dihydroxy-15-({2S}-1,3-benzodioxan-6-chloro-2-yl)-16,17,18,19,20-pentanor-5,13-prostadienoic acid (4-phenyl)-phenacylester of (5Z,10Z,13E)-(8R,12S,15R)-9-oxo-15-hydroxy-15-({2R}-1,3-benzodioxan-6-bromo-2-yl)-16,17,18,19,20-pentanor-5,10,13-prostatrienoic acid methylsulfamid of (8R,11R,12R,15R)-9-oxo-11,15-dihydroxy-15-({2RS}-1,3-benzodioxan-6,8-dichloro-2-yl)-16,17,18,19,20-pentanor-prostanoic acid Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

(5Z,13E)-(8R,9S,11R,12R,15R)-9,11,15-Trihydroxy-15-({2RS}-1,3-benzodioxan-2-yl)-16,17,18,19,20-pentanor-prostadienoic Acid and the Methyl Ester Thereof General Formula I: A=trans-CH=CH; B=cis-CH=CH;

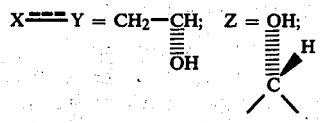

$R_1$=OCH$_3$, OH; $R_2$, $R_3$, $R_4$=H; the OH-group on C-15 is in the α-position.

(a) Methyl Ester of 1,3-Benzodioxane-2-carboxylic Acid

Under ice water cooling, a solution of 12.4 g. of saligenin in 100 ml. of dimethylformamide was added dropwise to a suspension of 9.6 g. of 50% sodium hydride in 100 ml. of dimethylformamide. The reaction mixture was stirred overnight at room temperature.

Under ice cooling, 9 ml. of dichloroacetic acid was introduced into 50 ml. of dimethylformamide. A suspension of 5.3 g. of 50% strength sodium hydride in 150 ml. of dimethylformamide was added thereto under ice cooling. The sodium hydride can also be added without a solvent.

This sodium dichloroacetate solution was introduced dropwise at room temperature into the first-prepared saligenin disodium solution. The reaction mixture was agitated at 60° C. for a total of 5 hours, adding potassium iodide thereto. During the last three hours, the dimethylformamide was distilled off with an oil pump. The semisolid, brown residue was acidified with concentrated-aqueous citric acid solution to pH 3 and extracted with methylene chloride. The organic phase was dried over magnesium sulfate, concentrated on a forced circulation evaporator, and combined at about 10° C. with diazomethane solution. After 1 hour of agitation at room temperature, the excess diazomethane and the solvent were removed by means of a water-jet aspirator. The remaining substance was introduced into saturated sodium chloride solution, extracted with methylene chloride, and the organic phase was dried with magnesium sulfate, concentrated, and purified by column chromatography on silica gel with hexane/5-10% ethyl acetate. Yield: 6 g. of the methyl ester of 1,3-benzodioxane-2-carboxylic acid; m.p. 28°-29° C.

(b) [2-Oxo-2-(1,3-benzodioxan-2-yl)-ethylidene]triphenylphosphorane

At room temperature under an argon atmosphere, 40 ml. of a 2.52-molar butyllithium solution in hexane was added dropwise to a suspension of 39 g. of triphenylmethylphosphonium bromide in 250 ml. of absolute ether; the reaction mixture was stirred for 15 hours, likewise under argon and at room temperature. A solution of 9.78 g. of the methyl ester of 1,3-benzodioxane-2-carboxylic acid in 100 ml. of absolute ether was added dropwise to the yellow gold solution, and the mixture was agitated for 1 hour at room temperature. The white precipitate was then filtered off, dissolved in water, and extracted with ether. The organic phase was combined with the filtrate, washed with water, dried over magnesium sulfate, and evporated to dryness. The residue was purified by column chromatography on silica gel with hexane/20-100% ethyl acetate and then recrystallized from ethyl acetate.

Yield: 12 g., m.p. 95°-98° C.

(c) (1S,5R,6R,7R)-6-[(E)-3-Oxo-3-({2RS}-1,3-benzodioxan-2-yl)-1-propenyl]-7-benzoyloxy-2-oxabicyclo[3,3,0]octan-3-one Under an argon atmosphere, 7 g. of (1S,5R,6R,7R)-6-formyl-7-benzoyloxy-2-oxabicyclo[3,3,0]octan-3-one, E. J. Corey et al., J. Amer. Chem. Soc. 91, 5675 (1969), and 11.2 g. of [2-oxo-2-(1,3-benzodioxan-2-yl)-ethylidene]-triphenylphosphorane were agitated at room temperature for 16 hours in 300 ml. of benzene. The reaction mixture was then evaporated to dryness under vacuum. The residue was purified by column chromatography on silica gel with hexane/20-60% ethyl acetate as the eluent. Yield: 5 g. of an oil.

(d) (1S,5R,6R,7R,3'R)-6-[(E)-3-Hydroxy-3-({2RS}-1,3-benzodioxan-2-yl)-1-propenyl]-7-benzoyloxy-2-oxabicyclo[3,3,0]octan-3-one A solution of 2 g. of the ketone obtained according to (c) in 140 ml. of absolute dimethoxyethane was combined with 140 ml. of ethereal zinc borohydride solution (preparation: "Neuere Methoden der praeparativen organischen Chemie" (More Recent Methods of Preparative Organic Chemistry), 4: 241, publishers: Verlag Chemie) and agitated under argon for 2 hours at room temperature. After dilution with 100 ml. of ether, the reaction solution was carefully combined with water, extracted with saturated sodium chloride solution, dried over magnesium sulfate, and concentrated to dryness under vacuum. The reaction products were separated by column chromatography on silica gel with hexane/30–60% ethyl acetate as the eluent. The α-alcohol was eluted as the first product; yield: 0.8 g.

(e)

(2RS,3aR,4R,5R,6aS,3'R)-4-[(E)-Hydroxy-3-({2RS}-1,3-benzodioxan-2-yl)-1-propenyl]-5-hydroxyperhydrocyclopenta[b]furan-2-ol General Formula II: A=trans-CH=CH; $R_2$, $R_3$, $R_4$, $R_5$, $R_6$=hydrogen atoms; the OH-group on C-3' is in the α-position.

Under argon, 5.5 ml. of a 20% solution of diisobutylaluminum hydride in toluene was added to a solution, cooled to −60° C., of 550 mg. of the lactone alcohol produced in accordance with (d) in 20 ml. of absolute toluene; the mixture was stirred at −60° C. for 30 minutes, and the reaction was then terminated by the dropwise addition of 2 ml. of isopropanol. After adding 20 ml. of water, the mixture was stirred for 15 minutes at 0° C., then extracted with ethyl acetate and/or methylene chloride, shaken with saturated sodium chloride solution, dried over magnesium sulfate, and concentrated to dryness under vacuum. Yield: 520 mg. of the crude product of the above lactol which was utilized without further purification for the next stage.

(f)

(5Z,13E)-(8R,9S,11R,12R,15R)-9,11,15-Trihydroxy-15-({2RS}-1,3-benzodioxan-2-yl)-16,17,18,19,20-pentanorprostadienoic Acid General Formula I: A=trans-CH=CH; B=cis-CH=CH;

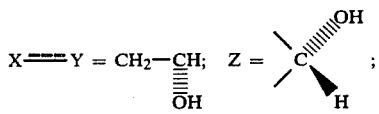

$R_1$=OH; $R_2$, $R_3$, $R_4$=H; the OH-group on C-15 is in the α-position.

A solution of 3.46 g. of 4-carboxybutyltriphenylphosphonium bromide in 10 ml. of absolute dimethyl sulfoxide (DMSO) was combined with 14.98 ml. of a solution of methanesulfinylmethylsodium in absolute DMSO (preparation: 2 g. of 50% sodium hydride suspension was dissolved in 40 ml. of absolute DMSO at 70° C.); the mixture was agitated for 30 minutes at room temperature. This solution, a reddish-brown color, was added dropwise under water cooling to a solution of 520 mg. of the lactol obtained according to (e) in 5 ml. of absolute DMSO. The reaction mixture was then stirred for 2 hours under argon at 50° C., and thereafter most of the DMSO was removed by distillation on an oil pump (bath temperature 40°–50° C.). The residue was combined with 50 ml. of ice water and extracted three times with ether. This ether extract was discarded. The aqueous phase was acidified to pH 4 with 10% citric acid solution, and then extracted four times with an ether/hexane mixture (1:1) and three times with methylene chloride. The organic phases were washed with saturated sodium chloride solution, dried over magnesium sulfate, and evaporated to dryness. The residue was purified by chromatography on silica gel with methylene chloride/1–10% ethanol as the eluent. Yield: 310 mg.

(g) The prostaglandin acid obtained according to (f) was dissolved in methylene chloride and esterified with ethereal diazomethane solution. The residue of the evaporation was chromatographed on silica gel with methylene chloride/4% isopropanol as the eluent, thus obtaining the methyl ester of pro glandin-carboxylic acid set forth as Example 1.

Yield: 288 mg.
$[\alpha]_D^{23}$ = +0.8° (c=0.25; CHCl$_3$)
IR: 3400 (broad), 1730, 1590, 1490, 980, 750 cm$^{-1}$.

EXAMPLE 2

(5Z,13E)-(8R,9S,11R,12R,15S)-9,11,15-Trihydroxy-15-({2RS}1,3-benzodioxan-2-yl)-16,17,18,19,20-pentanorprostadienoic acid and the Methyl Ester Thereof General Formula I: A=trans-CH=CH; B=cis-CH=CH;

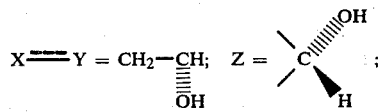

$R_1$=OCH$_3$, OH; $R_2$, $R_3$, $R_4$=hydrogen atoms; the OH-group on C-15 is in the β-position.

During the reaction of (1S,5R,6R,7R)-6-[(E)-3-oxo-3-({2RS}-1,3-benzodioxan-2-yl)-1-propenyl]-7-benzoyloxy-2-oxabicyclo[3,3,0]octan-3-one, described in Example 1(d), the β-alcohol was eluted from the column as the second product:

(a)

(1S,5R,6R,7R,3'S)-6-[(E)-3-Hydroxy-3-({2RS}-1,3-benzodioxan-2-yl)-1-propenyl]-7-benzoyloxy-2-oxabicyclo[3,3,0]octan-3-one Yield: 0.5 g.

(b)

(2RS,3aR,4R,5R,6aS,3'S)-4-[(E)-3-Hydroxy-3-({2RS}-1,3-benzodioxan-2-yl)-1-propenyl]-5-hydroxyperhydrocyclopenta[b]furan-2-ol General Formula II: A=trans-CH=CH; $R_2$, $R_3$, $R_4$, $R_5$, $R_6$=H; the OH-group on C-3' is in the β-position.

410 mg. of the β-alcohol obtained in accordance with (a) was reacted analogously to the description of Example 1(e) with diisobutylaluminum hydride, thus obtaining 400 mg. of a crude product.

(c)

(5Z,13E)-(8R,9S,11R,12R,15S)-9,11,15-Trihydroxy-15-({2RS}-1,3-benzodioxan-2-yl)-16,17,18,19,20-pentanorprostadienoic Acid General Formula I: A=trans-CH=CH; B=cis-CH=CH;

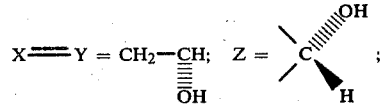

$R_1$=OH; $R_2$, $R_3$, $R_4$=H; the OH-group on C-15 is in the β-position.

The 400 mg. of lactol obtained in (b) was reacted without any further purification analogously to the procedure set forth in Example 1(f) with 2.66 g. of 4-carboxybutyltriphenylphosphonium bromide and 11.52 ml. of the methanesulfinylmethylsodium solution described in that example.

Yield: 220 mg.

(d) The prostaglandin acid obtained in accordance with (c) was dissolved in methylene chloride and esterified with ethereal diazomethane solution. The residue of the evaporation was chromatographed on silica gel with methylene chloride/4% isopropanol as the eluent, thus obtaining the prostaglandincarboxylic acid methyl ester set forth as Example 2.

Yield: 198 mg.

$[\alpha]_D^{23} = -0.8°$ (c=0.25; CHCl$_3$)

IR: 3400 (broad), 1730, 1590, 1490, 980, 750 cm$^{-1}$.

EXAMPLE 3

(5Z,13E)-(8R,9S,11R,12R,15R)-9,11,15-Trihydroxy-15-({2R}-1,3-benzodioxan-2-yl)-16,17,18,19,20-pentanor-prostadienoic Acid and the Methyl Ester Thereof General Formula I: A=trans-CH=CH; B=cis-CH=CH;

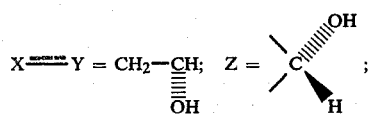

R$_1$=OCH$_3$, OH; R$_2$, R$_3$, R$_4$=H; the OH-group on C-15 is in the α-position.

(a)

(1S,5R,6R,7R)-6-[(E)-3-Oxo-3-({2R}-1,3-benzodioxan-2-yl)-1-propenyl]-7-benzoyloxy-2-oxabicyclo[3,3,0]octan-3-one The compound was obtained in the form of colorless crystals by benzene/ether crystallization of the oil described in Example 1(c); m.p.: 129°–130° C.; $[\alpha]_D^{23} = -147.4°$ (CHCl$_3$).

(b)

(1S,5R,6R,7R,3'R)-6-[(E)-3-Hydroxy-3-({2R}-1,3-benzodioxan-2-yl)-1-propenyl]-7-benzoyloxy-2-oxabicyclo[3,3,0]octan-3-one According to Example 1(d), the α-alcohol was obtained from 1.5 g. of the ketone obtained according to Example 3(a) as the first product of the column chromatography by zinc borohydride reduction. Yield: 0.61 g.; $[\alpha]_D^{23} = -101.3°$ (CHCl$_3$).

(c)

(2RS,3aR,4R,5R,6aS,3'R)-4-[(E)-3-Hydroxy-3-({2R}-1,3-benzodioxan-2-yl)-1-propenyl]-5-hydroxyperhydrocyclopenta[b]furan-2-ol General Formula II: A=trans-CH=CH; R$_2$, R$_3$, R$_4$, R$_5$, R$_6$=hydrogen atoms; the OH-group on C-3' is in the α-position.

Analogously to the directions given in Example 1(e), 600 mg. of the α-alcohol obtained according to (b) is reacted with diisobutylaluminum hydride, thus obtaining 450 mg. of a crude product.

(d)

(5Z,13E)-(8R,9S,11R,12R,15R)-9,11,15-Trihydroxy-15-({2R}-1,3-benzodioxan-2-yl)-16,17,18,19,20-pentanor-prostadienoic Acid General Formula I: A=trans-CH=CH; B=cis-CH=CH;

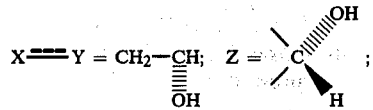

R$_1$=OH; R$_2$, R$_3$, R$_4$=hydrogen atoms; the OH-group on C-15 is in the α-position.

The 450 mg. of lactol obtained in (c) were reacted without further purification analogously to the directions in Example 1(f) with 3.8 g. of 4-carboxybutyltriphenylphosphonium bromide and 16.5 ml. of the methanesulfinylmethylsodium solution described therein. Yield: 315 mg.

(e) The prostaglandin acid obtained in accordance with (d) was dissolved in methylene chloride and esterified with ethereal diazomethane solution. The residue of the evaporation was chromatographed on silica gel with methylene chloride/1–6% isopropanol as the eluent, thus obtaining the methyl ester of the prostaglandin-carboxylic acid set forth as Example 3. Yield: 299 mg.

$[\alpha]_D^{23} = -21.2°$ (c=0.4; CHCl$_3$)

IR: 3400 (broad), 1730, 1590, 1490, 980, 750 cm$^{-1}$.

EXAMPLE 4

(5Z,13E)-(8R,9S,11R,12R,15S)-9,11,15-Trihydroxy-15-({2R}-1,3-benzodioxan-2-yl)-16,17,18,19,20-pentanor-prostadienoic Acid and the Methyl Ester Thereof General Formula I: A=trans-CH=CH; B=cis-CH=CH;

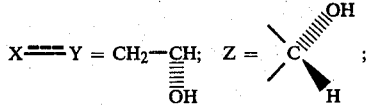

R$_1$=OCH$_3$, OH; R$_2$, R$_3$, R$_4$=hydrogen atoms; the OH-group on C-15 is in the β-position.

The β-alcohol was eluted from the column as the second product during the zinc borohydride reduction, disclosed under 3(b), of (1S,5R,6R,7R)-6-[(E)-3-oxo-3-({2R}-1,3-benzodioxan-2-yl)-1-propenyl]-7-benzoyloxy-2-oxabicyclo[3,3,0]octan-3-one (Example 3[a]):

(a)

(1S,5R,6R,7R,3'S)-6-[(E)-3-Hydroxy-3-({2R}-1,3-benzodioxan-2-yl)-1-propenyl]-7-benzoyloxy-2-oxabicyclo[3,3,0]octan-3-one Yield: 0.41 g.; $[\alpha]_D^{23} = -128°$ (CHCl$_3$).

(b)

(2RS,3aR,4R,5R,6aS,3'S)-4-[(E)-3-Hydroxy-3-({2R}-1,3-benzodioxan-2-yl)-1-propenyl]-5-hydroxyperhydrocyclopenta[b]furan-2-ol General Formula II: A=trans-CH=CH; R$_2$, R$_3$, R$_4$, R$_5$, R$_6$=hydrogen atoms; the OH-group on C-3' is in the β-position.

Following the description of Example 1(e), 410 mg. of the β-alcohol obtained according to (a) was reacted with diisobutylaluminum hydride, thus obtaining 400 mg. of a crude product.

(c)
(5Z,13E)-(8R,9S,11R,12R,15S)-9,11,15-Trihydroxy-15-({2R}-1,3-benzodioxan-2-yl)-16,17,18,19,20-pentanor-prostadienoic Acid General Formula I: A=trans-CH=CH; B=cis-CH=CH;

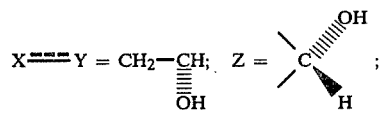

$R_1$=OH; $R_2$, $R_3$, $R_4$=hydrogen atoms; the OH-group on C-15 is in the β-position.

Analogously to the directions of Example 1(f), the 400 mg. of lactol obtained in (b) was reacted without any further purification with 2.66 g. of 4-carboxybutyl-triphenylphosphonium bromide and 11.52 ml. of the methanesulfinylmethylsodium solution described therein. Yield: 230 mg.

(d) The prostaglandin acid obtained according to (c) was dissolved in methylene chloride and esterified with ethereal diazomethane solution. The residue of the evaporation was chromatographed on silica gel with methylene chloride/1–6% isopropanol as the eluent, thus obtaining the prostaglandin-carboxylic acid methyl ester indicated as Example 4.

Yield: 212 mg. $[\alpha]_D^{23}$= −46.4° (c=0.25; CHCl₃).
IR: 3400 (broad), 1730, 1590, 1490, 980, 750 cm⁻¹.

EXAMPLE 5

(5Z,13E)-(8R,9S,11R,12R,15R)-9,11,15-Trihydroxy-15-({2S}-1,3-benzodioxan-2-yl)-16,17,18,19,20-pentanor-prostadienoic Acid and the Methyl Ester Thereof General Formula I: A=trans-CH=CH; B=cis-CH=CH;

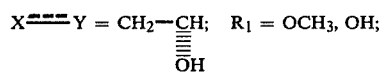

$R_2$, $R_3$, $R_4$=H; the OH-group on C-15 is in the α-position.

(a)
(1S,5R,6R,7R)-6-[(E)-3-Oxo-3-({2S}-1,3-benzodioxan-2-yl)-1-propenyl]-7-benzoyloxy-2-oxabicyclo[3,3,0]octan-3-one The mother liquor obtained according to Example 3(a) was chromatographed by column chromatography on silica gel with hexane/20–50% ethyl acetate as the eluent.

$[\alpha]_D^{23}$= −18.8° (CHCl₃).

(b)
(1S,5R,6R,7R,3′R)-6-[(E)-3-Hydroxy-3-({2S}-1,3-benzodioxan-2-yl)-1-propenyl]-7-benzoyloxy-2-oxabicyclo[3,3,0]octan-3-one According to Example 1(d), 3 g. of the ketone obtained as described in Example 5(a) was used for producing, by zinc borohydride reduction, the α-alcohol as the first product isolated by repeated conducted column chromatography.

Yield: 1.1 g.

(c)
(2RS,3aR,4R,5R,6aS,3′R)-4-[(E)-3-Hydroxy-3-({2S}-1,3-benzodioxan-2-yl)-1-propenyl]-5-hydroxyperhydrocyclopenta[b]furan-2-ol General Formula II: A=trans-CH=CH; $R_2$, $R_3$, $R_4$, $R_5$, $R_6$=H; the OH-group on C-3′ is in the α-position.

Analogously to the disclosure in Example 1(e), 800 mg. of the α-alcohol obtained according to Example 5(b) was reacted with diisobutylaluminum hydride, thus producing 750 mg. of a crude product.

(d)
(5Z,13E)-(8R,9S,11R,12R,15R)-9,11,15-Trihydroxy-15-({2S}-1,3-benzodioxan-2-yl)-16,17,18,19,20-pentanor-prostadienoic Acid General Formula I: A=trans-CH=CH; B=cis-CH=CH;

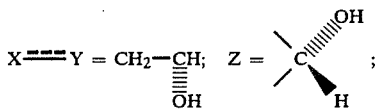

$R_1$=OH; $R_2$, $R_3$, $R_4$=H; the OH-group on C-15 is in the α-position.

The 750 mg. of lactol obtained in (c) was reacted without further purification, analogously to the directions in Example 1(f), with 5.1 g. of 4-carboxybutyltriphenylphosphonium bromide and 22 ml. of the methanesulfinylmethylsodium solution described therein.

Yield: 480 mg.

(e) The prostaglandin acid obtained in accordance with (d) was dissolved in methylene chloride and esterified with ethereal diazomethane solution. The residue of the evaporation was chromatographed on silica gel with hexane/50–95% ethyl acetate as the eluent, thus obtaining the prostaglandin-carboxylic acid methyl ester indicated as Example 5.

Yield: 450 mg.
$[\alpha]_D^{23}$= +51.2° (c=0.5; CHCl₃)
IR: 3400 (broad), 1730, 1590, 1490, 980, 750 cm⁻¹.

EXAMPLE 6

(5Z,13E)-(8R,9S,11R,12R,15S)-9,11,15-Trihydroxy-15-({2S}-1,3-benzodioxan-2-yl)-16,17,18,19,20-pentanor-prostadienoic Acid and the Methyl Ester Thereof General Formula I: A=trans-CH=CH; B=cis-CH=CH;

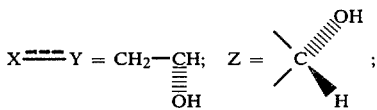

$R_1$=OCH₃,OH; $R_2$, $R_3$, $R_4$=H; the OH-group on C-15 is in the β-position.

During the zinc borohydride reduction, described in Example 5(b), of (1S,5R,6R,7R)-(6-[(E)-3-oxo-3-({2S}-1,3-benzodioxan-2-yl)-1-propenyl]-7-benzoyloxy-2-oxabicyclo[3,3,0]-octan-3-one (Example 5[a]), the β-alcohol was eluted as the second product from the column:

(a)
(1S,5R,6R,7R,3′S)-6-[(E)-3-Hydroxy-3-({2S}-1,3-benzodioxan-2-yl)-1-propenyl]-7-benzoyloxy-2-oxabicyclo[3,3,0]octan-3-one Yield: 0.7 g.

(b)
(2RS,3aR,4R,5R,6aS,3′S)-4-[(E)-3-Hydroxy-3-({2S}-1,3-benzodioxan-2-yl)-1-propenyl]-5-hydroxyperhydrocyclopenta[b]furan-2-ol General Formula II: A=trans-CH═CH; $R_2$, $R_3$, $R_4$, $R_5$, $R_6$=H; the OH-group on C-3′ is in the β-position.

600 mg. of the β-alcohol obtained according to Example 6(a) was reacted in accordance with Example 1(e) with diisobutylaluminum hydride, thus obtaining 470 mg. of a crude product.

(c)
(5Z,13E)-(8R,9S,11R,12R,15S)-9,11,15-Trihydroxy-15-({2S}-1,3-benzodioxan-2-yl)-16,17,18,19,20-pentanorprostadienoic Acid General Formula I: A=trans-CH═CH; B=cis-CH═CH;

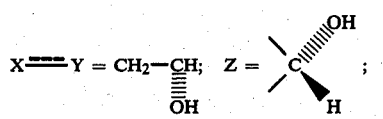

$R_1$=OH; $R_2$, $R_3$, $R_4$=H; the OH-group on C-15 is in the β-position.

The 470 mg. of lactol obtained in (b) was reacted without further purification analogously to the directions given in Example 1(f) with 3.8 g. of 4-carboxybutyltriphenylphosphonium bromide and 16.5 ml. of the methanesulfinylmethylsodium solution disclosed therein.

Yield: 330 mg.

(d) The prostaglandin acid obtained in accordance with (c) was converted analogously to Example 5(e) into the methyl ester of the prostaglandin-carboxylic acid.

Yield: 290 mg.
$[\alpha]_D^{23} = +50°$ (c=0.5; $CHCl_3$)
IR: 3400 (broad), 1730, 1590, 1490, 980, 750 $cm^{-1}$.

EXAMPLE 7

(5Z,13E)-(8R,11R,12R,15R)-11,15-Dihydroxy-9-oxo-15-({2RS}-1,3-benzodioxan-2-yl)-16,17,18,19,20-pentanorprostadienoic Acid and the Methyl Ester Thereof General Formula I: A=trans-CH═CH; B=cis-CH═CH;

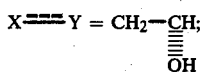

Z=C═O; $R_1$=$OCH_3$,OH; $R_2$, $R_3$, $R_4$=H; the OH-group on C-15 is in the β-position.

(a)
(1S,5R,6R,7R,3′R)-6-[(E)-3-Hydroxy-3-({2RS}-1,3-benzodioxan-2-yl)-1-propenyl]-7-hydroxy-2-oxabicyclo[3,3,0]octan-3-one A mixture of 1.97 g. of (1S,5R,6R,7R,3′R)-6-[(E)-3-hydroxy-({2RS}-1,3-benzodioxan-2-yl)-1-propenyl]-7-benzoyloxy-2-oxabicyclo[3,3,0]octan-3-one (prepared in accordance with Example 1[d]) and 622 mg. of potassium carbonate (anhydrous) in 91 ml. of methanol (absolute) was agitated at room temperature for 2 hours under argon. The mixture was then poured into 90 ml. of 0.1 N hydrochloric acid and extracted with ethyl acetate. The organic phase was washed with brine, dried with magnesium sulfate, and evaporated under vacuum. Chromatography of the crude product on silica gel (ether/ethyl acetate=7:3) yielded 1.20 g. of a colorless oil.

(b)
(1S,5R,6R,7R,3′R)-6-[(E)-3-({2RS}-1,3-Benzodioxan-2-yl)-1-propenyl]-3′,7-bis(tetrahydropyranyloxy)-2-oxabicyclo[3,3,0]octan-3-one At ice bath temperature, 6.1 ml. of freshly distilled dihydropyran and 15 mg. of p-toluenesulfonic acid were added to a solution of 1.85 g. of the diol obtained according to (a) in 50 ml. of methylene chloride; the mixture was stirred for 15 minutes at this temperature, diluted with methylene chloride, and shaken with sodium carbonate solution. The organic phase was washed with water, dried with magnesium sulfate, and evaporated under vacuum. After chromatography on silica gel (ether), 2.2 g. of the bis(tetrahydropyranyl)ether was obtained.

(c)
(2RS,3aR,4R,5R,6aS,3′R)-4-[(E)-3-({2RS}-1,3-Benzodioxan-2-yl)-1-propenyl]-3′,5-bis(tetrahydropyranyloxy)perhydrocyclopenta[b]furan-2-ol General Formula II: A=trans-CH═CH; $R_2$, $R_3$, $R_4$=H; $R_5$, $R_6$=THP; the OTHP-group on C-3′ is in the α-position.

Under argon, 22 ml. of a 20% DIBAH solution in toluene was added dropwise to a solution of 2.2 g. of the lactone obtained according to (b) in 85 ml. of absolute toluene, cooled to −70° C. After thirty minutes, the reaction was terminated by the dropwise addition of isopropanol, and the mixture was stirred for 15 minutes at 0° C. while adding 30 ml. of water. Thereafter, the reaction mixture was extracted with ethyl acetate, washed with brine, dried with magnesium sulfate, and evaporated under vacuum, thus obtaining 2.2 g. of lactol as a colorless oil.

(d)
(5Z,13E)-(8R,9S,11R,12R,15R)-9-Hydroxy-11,15-bis(tetrahydropyranyloxy)-15-({2RS}-1,3-benzodioxan-2-yl)-16,17,18,19,20-pentanorprostadienoic Acid A solution of 9.5 g. of 4-carboxybutyltriphenylphosphonium bromide in 40 ml. of absolute dimethyl sulfoxide was combined with 34.7 ml. of a solution of methanesulfinylmethylsodium in absolute dimethyl sulfoxide which was added dropwise (solution: 2.5 g. of 50% sodium hydride suspension was agitated in 50 ml. of absolute dimethyl sulfoxide for 1 hour at 70° C.). The mixture was stirred for 30 minutes at room temperature. This ylid solution was subsequently added dropwise at 15° C. to a solution of 2.16 g. of the lactol obtained according to (c) in 40 ml. of absolute dimethyl sulfoxide within 15 minutes; the mixture was then stirred for 2 hours at 50° C. Thereafter, the solvent was removed by distillation under an oil pump vacuum and at 45° C.; the residue was taken up in 80 ml. of water and extracted three times with ether. The organic extract was discarded. The aqueous phase was acidified with 10% citric acid solution to pH 4–5 and extracted four times with a mixture of hexane/ether 1+1. The ether/hexane extract was washed with brine, dried with magnesium sulfate, and evaporated under vacuum. After chromatographing the residue of the evaporation on silica gel, 2.48 g. of the acid was eluted with ether as a colorless oil.

(e)
(5Z,13E)-(8R,11R,12R,15R)-9-Oxo-11,15-bis(tetrahydropyranyloxy)-15-({2RS}-1,3-benzodioxan-2-yl)-16,17,18,19,20-pentanorprostadienoic Acid A solution of 2.35 g. of the alcohol obtained according to (d) in 30 ml. of acetone was combined at −20° C. with 2.46 ml. of Jones reagent (J.Chem.Soc. 1953, 2555) and agitated for 30 minutes at −20° C. Thereafter, 3 ml. of isopropyl alcohol was added dropwise to the reaction mixture and the latter was stirred for 10 minutes at −20° C., then diluted with ether, and shaken three times with water. The organic phase was dried with magnesium sulfate and evaporated under vacuum, thus obtaining 2.1 g. of the ketone as a colorless oil.

(f)
(5Z,13E)-(8R,11R,12R,15R)-11,15-Dihydroxy-9-oxo-15-({2RS}-1,3-benzodioxan-2-yl)-16,17,18,19,20-pentanorprostadienoic Acid General Formula I: A=trans-CH=CH; B=cis-CH=CH;

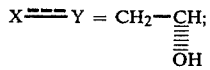

$Z=C=O$; $R_1=OH$; $R_2$, $R_3$, $R_4=H$; the OH-group on C-15 is in the α-position.

2.1 g. of the bis(tetrahydropyranyl)ether obtained according to (e) was agitated for 5 hours at 40° C. in 42 ml. of a mixture consisting of 65 parts of glacial acetic acid, 35 parts of water, and 10 parts of tetrahydrofuran. Thereafter, the mixture was evaporated to dryness at 0.1 torr and the crude product was purified by column chromatography. With chloroform/ethanol 95+5, 450 mg. of the E₂ derivative was eluted as a colorless oil.

(g) At ice bath temperature, 7 ml. of an ethereal diazomethane solution was added dropwise to a solution of 130 mg. of the acid obtained according to (f) in 4 ml. of methylene chloride; the mixture was agitated for 2 minutes and then evaporated under vacuum. After chromatography of the crude product on silica gel (ether/dioxane 95:5), 56 mg. of the prostaglandin-carboxylic acid methyl ester set forth as Example 7 was obtained, in addition to mixed fractions, in the form of an oil which was completely uniform according to thin-layer chromatography.

IR: 3400 (broad), 1740, 1730, 1590, 1490, 980, 750 cm$^{-1}$

EXAMPLE 8

(5Z,13E)-(8R,11R,12R,15S)-11,15-Dihydroxy-9-oxo-15-({2RS}-1,3-benzodioxan-2-yl)-16,17,18,19,20-pentanorprostadienoic Acid and the Methyl Ester Thereof General Formula I: A=trans-CH=CH; B=cis-CH=CH;

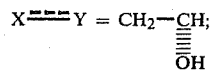

$Z=C=O$; $R_1=OCH_3,OH$; $R_2$, $R_3$, $R_4=H$; the OH-group on C-15 is in the β-position.

(a)
(1S,5R,6R,7R,3'S)-6-[(E)-3-Hydroxy-3-({2RS}-1,3-benzodioxan-2-yl)-1-propenyl]-7-hydroxy-2-oxabicyclo[3,3,0]octan-3-one 2.16 g. of (1S,5R,6R,7R,3'S)-6-[(E)-3-hydroxy-({2RS}-1,3-benzodioxan-2-yl)-1-propenyl]-7-benzoyloxy-2-oxabicyclo[3,3,0]octan-3-one (prepared according to Example 2[a]) and 687 mg. of anhydrous potassium carbonate was agitated for 2.5 hours in 99 ml. of methanol at room temperature. The reaction mixture was then combined with 99 ml. of 0.1 N HCl, agitated for 15 minutes, extracted with ethyl acetate, the organic phase was shaken with brine, dried, and evaporated under vacuum. The crude product was chromatographed on silica gel, thus obtaining 1.38 g. of the diol as a colorless oil.

(b)
(1S,5R,6R,7R,3'S)-6-[(E)-3-[{2RS}-1,3-Benzodioxan-2-yl)-1-propenyl]-3',7-bis(tetrahydropyranyloxy)-2-oxabicyclo[3,3,0]octan-3-one At ice bath temperature, 4.5 ml. of dihydropyran (freshly distilled) and 10 mg. of p-toluenesulfonic acid were added to a solution of 1.38 g. of the diol obtained according to (a) in 30 ml. of methylene chloride; the mixture was stirred for 15 minutes at about 5° C., diluted with methylene chloride, shaken with sodium bicarbonate solution, washed with brine, dried with magnesium sulfate, and evaporated under vacuum. After chromatographing the crude product on silica gel (ether/hexane 8:2), 1.91 g. of the bis(tetrahydropyranyl)ether was obtained as a colorless oil.

(c)
(2RS,3aR,4R,5R,6aS,3'S)-4-[(E)-3-({2RS}-1,3-Benzodioxan-2-yl)-1-propenyl]-3',5-bis(tetrahydropyranyloxy)-perhydrocyclopenta[b]furan-2-ol General Formula II: A=trans-CH↑CH; $R_2$, $R_3$, $R_4=H$; $R_5$, $R_6=THP$; the OTHP-group on C-3' is in the β-position.

Analogously to the directions in Example 7(c), 1.91 g. of the lactone produced according to (b) in 75 ml. of absolute toluene was reduced with 19 ml. of diisobutylaluminum hydride solution (DIBAH solution). After working up the reaction mixture as usual, 1.93 g. of lactol was obtained as a colorless oil.

(d)
(5Z,13E)-(8R,9S,11R,12R,15S)-9-Hydroxy-11,15-bis(tetrahydropyranyloxy)-15-({2RS}-1,3-benzodioxan-2-yl)-16,17,18,19,20-pentanorprostadienoic Acid Analogously to the disclosure in Example 7(d), 1.93 g. of the lactol produced in accordance with (c) in 30 ml. of absolute DMSO was reacted with an ylene solution produced from 8.47 g. of 4-carboxybutyltriphenylphosphonium bromide and 31 ml. of methanesulfinylmethylsodium solution. After the usual work up, the crude product was purified by column chromatography. With ether, 2.1 g. of the acid was eluted as a colorless oil.

(e)
(5Z,13E)-(8R,11R,12R,15S)-9-Oxo-11,15-bis(tetrahydropyranyloxy)-15-({2RS}-1,3-benzodioxan-2-yl)-16,17,18,19,20-pentanorprostadienoic Acid In analogy to the directions given in Example 7(e), 2.05 g. of the alcohol obtained according to (d) in 50 ml. of acetone was oxidized with 2.14 ml. of Jones reagent at $-20°$ C. The mixture was worked up, thus producing 1.84 g. of the ketone as a colorless oil.

(f)
(5Z,13E)-(8R,11R,12R,15S)-11,15-Dihydroxy-9-oxo-15-({2RS}-1,3-benzodioxan-2-yl)-1,6,17,18,19,20-pentanorprostadienoic Acid General Formula I: A=trans-CH=CH; B=cis-CH=CH;

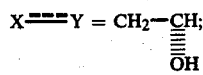

$Z=C=O$; $R_1=OH$; $R_2$, $R_3$, $R_4=H$; the OH-group on C-15 is in the $\beta$-position.

Analogously to the directions in Example 7(f), 1.84 g. of the bis(tetrahydropyranyl)ether obtained according to (e) was agitated with 18 ml. of the acetic acid/THF mixture. After working up the reaction mixture and chromatographing same on silica gel (chloroform/ethanol=95:5), 528 mg. of the $E_2$ derivative was obtained as a colorless oil.

(g) 98 mg. of the prostaglandin acid obtained according to (f) was converted into the prostaglandin-carboxylic acid methyl ester analogously to Example 7(g).

Yield: 76 mg.

IR: 3400 (broad), 1740, 1730, 1590, 1490, 980, 750 cm$^{-1}$

EXAMPLE 9
(5Z,13E)-(8R,11R,12R,15R)-11,15-Dihydroxy-9-oxo-15-({2R}-1,3-benzodioxan-2-yl)-16,17,18,19,20-pentanorprostadienoic Acid and the Methyl Ester Thereof General Formula I: A=trans-CH=CH; B=cis-CH=CH;

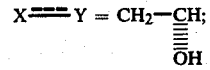

$Z=C=O$; $R_1=OCH_3,OH$; $R_2$, $R_3$, $R_4=H$; the OH-group on C-15 is in the $\alpha$-position.

These compounds are prepared analogously to Example 7(a)-(g) from the starting compound produced according to Example 3(b) Yield: 400 mg. of prostadienoic acid as a colorless oil; 60 mg. of the methyl ester of the prostadienoic acid (produced from 130 mg. of the acid).

IR: 3500-3400, 1740, 1730, 1590, 1490, 980, 750 cm$^{-1}$.

EXAMPLE 10
(5Z,13E)-(8R,11R,12R,15S)-11,15-Dihydroxy-9-oxo-15-({2R}-1,3-benzodioxan-2-yl)-16,17,18,19,20-pentanorprostadienoic Acid and the Methyl Ester Thereof General Formula I: A=trans-CH=CH; B=cis-CH=CH;

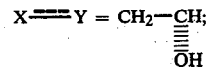

$Z=C=O$; $R_1=OCH_3$, OH; $R_2$, $R_3$, $R_4=H$; the OH-group on C-15 is in the $\beta$-position.

These compounds are prepared in analogy to Examples 8(a) (g) from the starting compound produced according to Example 4(a). Yield: 510 mg. of prostadienoic acid as a colorless oil; 70 mg. of the prostadienoic acid methyl ester (from 100 mg. of the acid).

IR: 3500-3400, 1740, 1730, 1590, 1490, 980, 750 cm$^{-1}$.

EXAMPLE 11
(5Z,13E)-(8R,11R,12R,15R)-11,15-Dihydroxy-9-oxo-15-({2S}-1,3-benzodioxan-2-yl)-16,17,18,19,20-pentanorprostadienoic Acid and the Methyl Ester Thereof General Formula I: A=trans-CH=CH; B=cis-CH=CH;

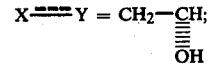

$Z=C=O$; $R_1=OCH_3$, OH; $R_2$, $R_3$, $R_4=H$; the OH-group on C-15 is in the $\alpha$-position.

These compounds are produced analogously to Examples 7(a)-(g) from the starting compound prepared according to Example 5(b).

Yield: 310 mg. of prostadienoic acid as a colorless oil; 50 mg. of the prostadienoic acid methyl ester (from 120 mg. of the acid).

IR: 3500-3400, 1740, 1730, 1590, 1490, 980, 750 cm$^{-1}$

EXAMPLE 12
5Z,13E)-(8R,11R,12R,15S)-11,15-Dihydroxy-9-oxo-15-({2S}-1,3-benzodioxan-2-yl)-16,17,18,19,20-pentanorprostadienoic Acid and the Methyl Ester Thereof General Formula I: A=trans-CH=CH; B=cis-CH=CH;

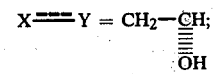

$Z=C=O$; $R_1=OCH_3$, OH; $R_2$, $R_3$, $R_4=H$; the OH-group on C-15 is in the $\beta$-position.

These compounds are prepared in analogy to Examples 8(a)-(g) from the starting compound produced according to Example 6(a).

Yield: 410 mg. of prostadienoic acid; 150 mg. of the prostadienoic acid methyl ester (from 210 mg. of the acid).

IR: 3500-3400, 1740, 1730, 1590, 1490, 980, 750 cm$^{-1}$.

EXAMPLE 13

(5Z)-(8R,9S,11R,12R,15R)-9,11,15-Trihydroxy-15-({2RS}-1,3-benzodioxan-2-yl)-16,17,18,19,20-pentanorprostenoic Acid and the Methyl Ester Thereof General Formula I: $A=CH_2-CH_2$; $B=cis-CH=CH$;

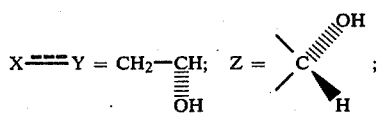

$R_1 = OCH_3, OH$; $R_2$, $R_3$, $R_4 = H$; the OH-group on C-15 is in the α-position.

(a)
(1S,5R,6R,7R,3'R)-6-[3-Hydroxy-3-({2S}-1,3-benzodioxan-2-yl)-1-propyl]-7-benzoyloxy-2-oxabicyclo[3,3,0]octan-3-one Under a hydrogen atmosphere, 2.3 g. of the α-alcohol obtained according to Example 1(d) and 230 mg. of palladium on charcoal (10%) was shaken for 2 hours in 40 ml. of ethyl acetate. After filtration and evaporation, 2.3 g. of the above alcohol was obtained as a colorless oil.

IR: 3600, 1775, 1720, 1590, 1490, 770 cm$^{-1}$.

No olefinic protons could be detected in the NMR spectrum.

(b)
(1S,5R,6R,7R,3'R)-6-[3-Hydroxy-3-({2RS}-1,3-benzodioxan-2-yl)-1-propyl]-7-hydroxy-2-oxabicyclo[3,3,0]octan-3-one By treatment according to Example 7(a), 1.34 g. of the saturated diol was obtained in the form of a colorless oil from 2.20 g. of the saturated alcohol obtained in accordance with (a).

IR: 3600 (strong), 1775, 1590, 1490, 760 cm$^{-1}$.

(c)
1S,5R,6R,7R,3'R)-6-[3-({2RS}-1,3-Benzodioxan-2-yl)-1-propyl]-3',7-bis(tetrahydropyranyloxy)-2-oxabicyclo[3,3,0]octan-3-one From 1.13 g. of the diol obtained according to (b), 1.08 g. of the above bis(tetrahydropyranyl)ether was obtained as a colorless oil from dihydropyran analogously to Example 7(b)

IR: 1775, 1590, 1490, 1100, 760 cm$^{-1}$.

(d)
(2RS,3aR,4R,5R,6aS,3'R)-4-[3-({2RS}-1,3-Benzodioxan-2-yl)-1-propyl]-3,5-bis(tetrahydropyranyloxy)perhydrocyclopenta[b]furan-2-ol General Formula II: $A=CH_2-CH_2$; $R_2$, $R_3$, $R_4=H$; $R_5$, $R_6=THP$; the OTHP-group on C-3' is in the α-position.

According to Example 7(c), 1.06 g. of the above lactol was produced as a colorless oil by the reduction of 1.08 g. of the bis(tetrahydropyranyl)ether prepared according to (c).

IR* 3600, 1590, 1490, 1100, 760 cm$^{-1}$.

(e)
(5Z)-(8R,9S,11R,12R,15R)-9-Hydroxy-11,15-bis-(tetrahydropyranyloxy)-15-({2RS}-1,3-benzodioxan-2-yl)-16,17,18,19,20-pentanorprostenoic Acid 1.06 g. of the lactol obtained according to (d) was converted according to Example 7(d) into 866 mg. of the above prostenoic acid.

IR: 3600–3400, 1710, 1590, 1490, 1100, 760 cm$^{-1}$.

(f)
(5Z)-(8R,9S,11R,15R)-9,11,15-Trihydroxy-15-({2RS}-1,3-benzodioxan-2-yl)-16,17,18,19,20-pentanorprostenoic Acid 310 mg. of the compound produced in accordance with (e) was agitated in 9 ml. of a mixture of acetic acid/water/tetrahydrofuran=65:35:10 for 3 hours at 50° C. The mixture was then evaporated to dryness under vacuum. Chromatograpy on 10 g. of silica gel (chloroform/ethanol 4+1) yielded 211 mg. of the above compound as a colorless oil.

IR: 3600–3300, 1710, 1590, 1490, 760 cm$^{-1}$.

(g) At ice bath temperature, 7 ml. of an ethereal diazomethane solution was added dropwise to a solution of 130 mg. of the acid obtained according to (f) in 4 ml. of methylene chloride; the mixture was agitated for 15 minutes and then evaporated under vacuum. After chromatography of the crude product on silica gel (methylene chloride/3% isopropanol), 90 mg. of the prostaglandin-carboxylic acid methyl ester set forth as Example 13 was obtained.

IR: 3600–3300, 1730, 1590, 1490, 760 cm$^{-1}$.

EXAMPLE 14

(5Z)-(8R,9S,11R,12R,15S)-9,11,15-Trihydroxy-15-({2RS}-1,3-benzodioxan-2-yl)-16,17,18,19,20-pentanorprostenoic Acid and the Methyl Ester Thereof General Formula I: $A=CH_2-CH_2$; $B=cis-CH=CH$;

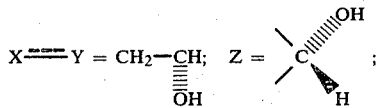

$R_1 = OCH_3, OH$; $R_2$, $R_3$, $R_4 = H$; the OH-group on C-15 is in the β-position.

(a)
(1S,5R,6R,7R,3'S)-6-[3-Hydroxy-3-({2RS}-1,3-benzodioxan-2-yl)-1-propyl]-7-benzoyloxy-2-oxabicyclo[3,3,0]octan-3-one Analogously to Example 13(a), 2.4 g. of the β-alcohol obtained according to Example 2(a) was hydrogenated to 2.4 g. of the above-mentioned saturated alcohol, obtained in the form of a colorless oil.

IR: 3600, 1775, 1720, 1590, 1490, 770 cm$^{-1}$.

(b)
(1S,5R,6R,7R,3'S)-6-[3-Hydroxy-3-({2RS}-1,3-benzodioxan-2-yl)-1-propyl]-7-hydroxy-2-oxabicyclo[3,3,0]octan-3-one By treatment with potassium carbonate according to Example 7(a), 1.39 g. of the saturated diol was produced as a colorless oil from 2.3 g. of the saturated alcohol obtained according to (a).

IR: 3600 (strong), 1775, 1590, 1490, 760 cm$^{-1}$.

(c)

(1S,5R,6R,7R,3'S)-6-[3-({2RS}-1,3-Benzodioxan-2-yl)-1-propyl]-3',7-bis(tetrahydropyranyloxy)-2-oxabicyclo[3,3,0]octan-3-one From 1.0 g. of the diol obtained according to (b), 0.93 g. of the above bis(tetrahydropyranyl)ether was produced as a colorless oil with dihydropyran analogously to Example 7(b).

IR: 1775, 1590, 1490, 1100, 760 cm$^{-1}$.

(d)

(2RS,3aR,4R,5R,6aS,3'S)-4-[3-({2RS}-1,3-Benzodioxan-2-yl)-1-propyl]-3',5-bis(tetrahydropyranyloxy)perhydrocyclopenta[b]furan-2-ol According to Example 7(c), reduction of 0.74 g. of the bis(tetrahydropyranyl)ether produced according to (c) yielded 0.7 g. of the above lactol as a colorless oil.

IR: 3600, 1590, 1490, 1100, 760 cm$^{-1}$.

(e)

(5Z)-(8R,9S,11R,12R,15S)-9-Hydroxy-11,15-bis(tetrahydropyranyloxy)-15-({2RS}-1,3-benzodioxan-2-yl)-16,17,18,19,20-pentanorprostenoic Acid According to Example 7(d), 0.7 g. of the lactol obtained as described in (d) was converted into 0.51 g. of the above prostenoic acid.

IR: 3600–3400, 1710, 1590, 1490, 1100, 760 cm$^{-1}$.

(f)

(5Z)-(8R,9S,11R,12R,15S)-9,11,15-Trihydroxy-15-({2RS}-1,3-benzodioxan-2-yl)-16,17,18,19,20-pentanorprostenoic Acid Analogously to the directions given in Example 13(f), 219 mg. of the above compound was obtained as a colorless oil from 345 mg. of the triol obtained according to (e).

IR: 3600–3300, 1710, 1590, 1490, 760 cm$^{-1}$.

(g) Analogously to the esterification step described in Example 13(g), 120 mg. of the acid produced according to (f) yielded 85 mg. of the prostaglandin-carboxylic acid methyl ester set forth as Example 14.

IR: 3600–3300, 1730, 1590, 1490, 755 cm$^{-1}$.

EXAMPLE 15

(5Z)-(8R,9S,11R,12R,15R)-9,11,15-Trihydroxy-15-({2R}-1,3-benzodioxan-2-yl)-16,17,18,19,20-pentanorprostenoic Acid and the Methyl Ester Thereof General Formula I: A=CH$_2$—CH$_2$; B=cis—CH=CH;

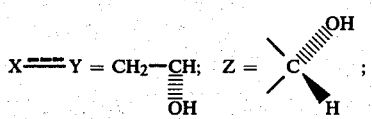

$R_1$=OCH$_3$,OH; $R_2$, $R_3$, $R_4$=H; the OH-group on C-15 is in the α-position.

Starting with the α-alcohol obtained according to Example 3(b), the title compounds were obtained analogously to the reaction stages described for Examples 13(a)–(g).

IR (Methyl ester): 3500–3300, 1730, 1590, 1490, 760 cm$^{-1}$.

EXAMPLE 16

(5Z)-(8R,9S,11R,12R,15S)-9,11,15-Trihydroxy-15-({2R}-1,3-benzodioxan-2-yl)-16,17,18,19,20-pentanorprostenoic Acid and the Methyl Ester Thereof General Formula I: A=CH$_2$—CH$_2$; B=cis—CH=CH;

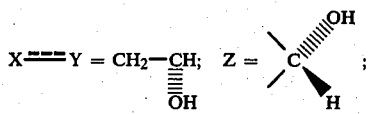

$R_1$=OCH$_3$,OH; $R_2$, $R_3$, $R_4$=H; the OH-group on C-15 is in the β-position.

Starting with the β-alcohol obtained according to Example 4(a), the title compounds were produced analogously to the reaction stages described for Examples 14(a)–(g).

IR (Methyl ester): 3400 (broad), 1730, 1590, 1490, 760 cm$^{-1}$.

EXAMPLE 17

(5Z)-(8R,9S,11R,12R,15R)-9,11,15-Trihydroxy-15-({2S}-1,3-benzodioxan-2-yl)-16,17,18,19,20-pentanorprostenoic Acid and the Methyl Ester Thereof General Formula I: A=CH$_2$—CH$_2$; B=cis—CH=CH;

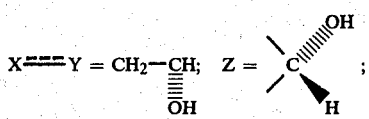

$R_1$=OCH$_3$,OH; $R_2$, $R_3$, $R_4$=H; the OH-group on C-15 is in the α-position.

Starting with the α-alcohol obtained according to Example 5(b), the title compounds were obtained analogously to the reaction stages described for Example 13(a)–(g).

IR (Methyl ester): 3400 (broad), 1735, 1590, 1490, 760 cm$^{-1}$.

EXAMPLE 18

(5Z)-(8R,9S,11R,12R,15S)-9,11,15-Trihydroxy-15-({2S}-1,3-benzodioxan-2-yl)-16,17,18,19,20-pentanorprostenoic Acid and the Methyl Ester Thereof General Formula I: A=CH$_2$—CH$_2$; B=cis—CH=CH;

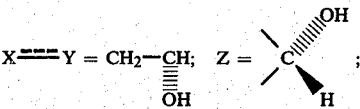

$R_1$=OCH$_3$,OH; $R_2$, $R_3$, $R_4$=H; the OH-group on C-15 is in the β-position.

Starting with the β-alcohol produced according to Example 6(a), the title compounds were obtained analogously to the reaction stages described in Examples 14(a)–(g).

IR (Methyl ester): 3400 (broad), 1735, 1590, 1490, 760 cm$^{-1}$.

EXAMPLE 19

(5Z)-(8R,11R,12R,15R)-11,15-Dihydroxy-9-oxo-15-({2RS}-1,3-benzodioxan-2-yl)-16,17,18,19,20-pentanorprostenoic Acid and the Methyl Ester Thereof General Formula I: $A=CH_2-CH_2$; $B=cis=CH=CH$;

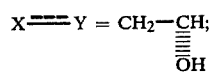

$Z=>C=O$; $R_1=OCH_3,OH$; $R_2$, $R_3$, $R_4=H$; the OH-group on C-15 is in the α-position.

(a) (5Z)-(8R,11R,12R,15R)-11,15-Bis(tetrahydropyranyloxy)-9-oxo-15-({2RS}-1,3-benzodioxan-2-yl)-16,17,18,19,20-pentanorprostenoic Acid Analogously to Example 7(e), 300 mg. of the compound obtained according to Example 13(e) was converted by oxidation into the above-mentioned compound, thus obtaining 210 mg. of the product as a colorless oil.

IR: 3600–3300, 1740, 1710, 1590, 1490, 760 cm$^{-1}$.

(b) (5Z)-(8R,11R,12R,15R)-11,15-Dihydroxy-9-oxo-15-({2RS}-1,3-benzodioxan-2-yl)-16,17,18,19,20-pentanorprostenoic Acid In accordance with Example 7(f), 150 mg. of the compound obtained according to (a) yielded 90 mg. of the above compound as a colorless oil.

IR: 3600–3400, 1740, 1710, 1590, 1490, 760 cm$^{-1}$.

(c) Analogously to Example 7(g), 90 mg. of the acid obtained according to (b) yielded 75 mg. of the prostaglandincarboxylic acid methyl ester.

IR: 3600–3400, 1740, 1730, 1590, 1490, 750 cm$^{-1}$.

EXAMPLE 20

(5Z)-(8R,11R,12R,15S)-11,15-Dihydroxy-9-oxo-15-({2RS}-1,3-benzodioxan-2-yl)-16,17,18,19,20-pentanorprostenoic Acid and the Methyl Ester Thereof General Formula I: $A=CH_2-CH_2$; $B=cis-CH=CH$;

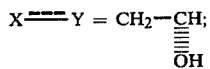

$Z=>C=O$; $R_1=OCH_3,OH$; $R_2$, $R_3$, $R_4=H$; the OH-group on C-15 is in the β-position.

(a) (5Z)-(8R,11R,12R,15S)-11,15-Bis(tetrahydropyranyloxy)-9-oxo-15-({2RS}-1,3-benzodioxan-2-yl)-16,17,18,19,20-pentanorprostenoic Acid By oxidation analogously to Example 7(e), 280 mg. of the compound obtained according to Example 14(e) was converted into the above compound, yielding 180 mg. as a colorless oil.

IR: 3600–3300, 1740, 1710, 1590, 1490, 760 cm$^{-1}$.

(b) (5Z)-(8R,11R,12R,15S)-11,15-Dihydroxy-9-oxo-15-({2RS}-1,3-benzodioxan-2-yl)-16,17,18,19,20-pentanorprostenoic Acid According to Example 7(f), 145 mg. of the compound produced according to (a) was converted to 80 mg. of the above diol.

IR: 3600–3400, 1740, 1710, 1590, 1490, 755 cm$^{-1}$.

(c) Analogously to Example 7(g), 80 mg. of the acid produced according to (b) yielded 56 mg. of the above-mentioned prostaglandin-carboxylic acid methyl ester.

IR: 3600–3400, 1740, 1730, 1590, 1490, 755 cm$^{-1}$.

EXAMPLE 21

(5Z)-(8R,11R,12R,15R)-11,15-Dihydroxy-9-oxo-15-({2R}-1,3-benzodioxan-2-yl)-16,17,18,19,20-pentanorprostenoic Acid and the Methyl Ester Thereof General Formula I: $A=CH_2-CH_2$; $B=cis-CH=CH$;

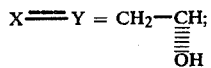

$Z=>C=O$; $R_1=OCH_3,OH$; $R_2$, $R_3$, $R_4=H$; the OH-group on C-15 is in the α-position.

Starting with the derivative of Example 15 corresponding to Example 13(e), the title compounds were obtained analogously to the reaction stages described for Examples 19(a)–(c).

IR (Methyl ester): 3500–3400, 1740, 1730, 1590, 1490, 750 cm$^{-1}$.

EXAMPLE 22

(5Z)-(8R,11R,12R,15S)-11,15-Dihydroxy-9-oxo-15-({2R}-1,3-benzodioxan-2-yl)-16,17,18,19,20-pentanorprostenoic Acid and the Methyl Ester Thereof General Formula I: $A=CH_2-CH_2$; $B=cis-CH=CH$;

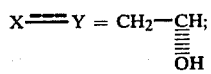

$Z=>C=O$; $R_1=OCH_3,OH$; $R_2$, $R_3$, $R_4=H$; the OH-group on C-15 is in the β-position.

Starting with the derivative of Example 16 corresponding to Example 14(e), the title compounds were obtained analogously to the reaction stages described for Examples 19(a)–(c).

IR (Methyl ester): 3600–3400, 1740, 1730, 1590, 1490, 755 cm$^{-1}$.

EXAMPLE 23

(5Z)-(8R,11R,12R,15R)-11,15-Dihydroxy-9-oxo-15-({2S}-1,3-benzodioxan-2-yl)-16,17,18,19,20-pentanorprostenoic Acid and the Methyl Ester Thereof General Formula I: $A=CH_2-CH_2$; $B=cis-CH=CH$;

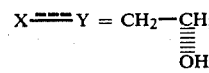

$Z=>C=O$; $R_1=OCH_3,OH$; $R_2$, $R_3$, $R_4=H$; the OH-group on C-15 is in the α-position.

Starting with the derivative of Example 17 corresponding to Example 13(e), the title compounds were produced in analogy to the reaction stages described for Examples 19(a)–(c).

IR (Methyl ester): 3600–3400, 1740, 1730, 1590, 1490, 755 cm$^{-1}$.

EXAMPLE 24

(5Z)-(8R,11R,12R,15S)-11,15-Dihydroxy-9-oxo-15-({2S}-1,3-benzodioxan-2-yl)-16,17,18,19,20-pentanorprostenoic Acid and the Methyl Ester Thereof General Formula I: $A=CH_2-CH_2$; $B=cis-CH=CH$;

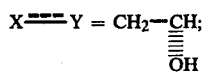

$Z=>C=O$; $R_1=OCH_3,OH$; $R_2$, $R_3$, $R_4=H$; the OH-group on C-15 is in the β-position.

Starting with the derivative of Example 18 corresponding to Example 14(e), the title compounds were produced in analogy to the reaction stages described for Example 19(a)–(c).

IR (Methyl ester): 3500–3400, 1740, 1730, 1590, 1490, 750 cm$^{-1}$.

EXAMPLE 25

(5Z,10Z,13E)-(8R,12S,15R)-15-Hydroxy-9-oxo-15-({2RS}-1,3-benzodioxan-2-yl)-16,17,18,19,20-pentanorprostatrienoic Acid and the Methyl Ester Thereof General Formula I: $A=trans-CH=CH$; $B=cis-CH=CH$; $X\equiv\equiv\equiv Y=CH=CH$; $Z=>C=O$; $R_1=OCH_3,OH$; $R_2$, $R_3$, $R_4=H$; the OH-group on C-15 is in the α-position.

A solution of 88 mg. of (5Z,13E)-(8R,11R,12R,15R)-11,15-dihydroxy-9-oxo-15-({2RS}-1,3-benzodioxan-2-yl)-16,17,18,19,20-pentanorprostadienoic acid (from Example 7[f]) in 6 ml. of 90% acetic acid was stirred for 19 hours at 60° C. and then evaporated under vacuum. Chromatography on silica gel (ether/3% dioxane) and subsequent etherification of the prostatrienoic acid with ethereal diazomethane solution yielded 45 mg. of the title compound as an oil having a slightly yellow coloring.

IR (Methyl ester): 3600–3300, 1730, 1700, 1590, 1490, 980, 760 cm$^{-1}$.

EXAMPLE 26

(5Z,10Z,13E)-(8R,12S,15S)-15-Hydroxy-9-oxo-15-({2RS}-1,3-benzodioxan-2-yl)-16,17,18,19,20-pentanorprostatrienoic Acid and the Methyl Ester Thereof General Formula I: $A=trans-CH=CH$; $B=cis-CH=CH$; $X\equiv\equiv\equiv Y=CH=CH$; $Z=>C=O$; $R_1=OCH_3,OH$; $R_2$, $R_3$, $R_4=H$; the OH-group on C-15 is in the β-position.

According to the directions given in Example 25, the title compounds were prepared from the compound described in Example 8(f).

IR (Methyl ester): 3500–3300, 1730, 1705, 1590, 1490, 980, 760 cm$^{-1}$.

EXAMPLE 27

(5Z,10Z,13E)-(8R,12S,15S)-15-Hydroxy-9-oxo-15-({2R}-1,3-benzodioxan-2-yl)-16,17,18,19,20-pentanorprostatrienoic Acid and the Methyl Ester Thereof General Formula I: $A=trans-CH=CH$; $B=cis-CH=CH$; $X\equiv\equiv\equiv Y=CH=CH$; $Z=>C=O$; $R_1=OCH_3,OH$; $R_2$, $R_3$, $R_4=H$; the OH-group on C-15 is in the α-position.

According to the directions given in Example 25, the title compounds were obtained from the compound disclosed in Example 9(f).

IR (Methyl ester): 3600–3300, 1730, 1700, 1585, 1490, 980, 760 cm$^{-1}$.

EXAMPLE 28

(5Z,10Z,13E)-(8R,12S,15S)-15-Hydroxy-9-oxo-15-({2R}-1,3-benzodioxan-2-yl)-16,17,18,19,20-pentanorprostatrienoic Acid and the Methyl Ester Thereof General Formula I: $A=trans-CH=CH$; $B=cis-CH=CH$; $X\equiv\equiv\equiv Y=CH=CH$; $Z=>C=O$; $R_1=OCH_3,OH$; $R_2$, $R_3$, $R_4=H$; the OH-group on C-15 is in the β-position.

According to the disclosure of Example 25, the title compounds were produced from the compound described in Example 10(f).

IR (Methyl ester): 3600–3300, 1730, 1700, 1590, 1490, 980, 760 cm$^{-1}$.

EXAMPLE 29

(5Z,10Z,13E)-(8R,12S,15R)-15-Hydroxy-9-oxo-15-({2S}-1,3-benzodioxan-2-yl)-16,17,18,19,20-pentanorprostatrienoic Acid and the Methyl Ester Thereof General Formula I: $A=trans-CH=CH$; $B=cis-CH=CH$; $X\equiv\equiv\equiv Y=CH=CH$; $Z=>C=O$; $R_1=OCH_3,OH$; $R_2$, $R_3$, $R_4=H$; the OH-group on C-15 is in the α-position.

According to the directions set forth in Example 25, the title compounds were produced from the compound described in Example 11(f).

IR(Methyl ester): 3500–3300, 1730, 1700, 1590, 1485, 980, 760 cm$^{-1}$.

EXAMPLE 30

(5Z,10Z,13E)-(8R,12S,15S)-15-Hydroxy-9-oxo-15-({2S}-1,3-benzodioxan-2-yl)-16,17,18,19,20-pentanorprostatrienoic Acid and the Methyl Ester Thereof General Formula I: $A=trans-CH=CH$; $B=cis-CH=CH$; $X\equiv\equiv\equiv Y=CH=CH$; $Z=>C=O$; $R_1=OCH_3,OH$; $R_2$, $R_3$, $R_4=H$; the OH-group on C-15 is in the β-position.

According to the directions given in Example 25, the title compounds were produced from the compound disclosed in Example 12(f).

IR (Metyhl ester): 3600–3300, 1730, 1700, 1590, 1490, 980, 760 cm$^{-1}$.

EXAMPLE 31

(13E)-(8R,9S,11R,12R,15R)-9,11,15-Trihydroxy-15-({2RS}-1,3-benzodioxan-2-yl)-16,17,18,19,20-pentanorprostenoic Acid and the Methyl Ester Thereof General Formula I: $A=trans-CH=CH$; $B=CH_2-CH_2$;

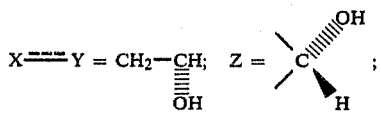

$R_1=OCH_3,OH$; $R_2$, $R_3$, $R_4=H$; the OH-group on C-15 is in the α-position.

150 mg. of the compound obtained according to Example 1(f) and Example 1(g), respectively, was mixed with 15 mg. of 10% palladium on charcoal and stirred with 15 ml. of ethyl acetate for 2 hours at −20° C. under a hydrogen atmosphere. After filtration, the reaction mixture was evaporated to dryness under vacuum, thus obtaining 140 mg. of the title compound as a colorless oil.

IR (Methyl ester): 3600–3300, 1730, 1590, 1490, 980, 760 cm$^{-1}$.

The NMR spectrum showed only two olefinic protons.

EXAMPLE 32

Analogously to Example 31, the following compounds can be produced from the corresponding starting compounds 2(d), 3(e), 4(d), 5(e), 6(d):

(13E)-(8R,9S,11R,12R,15S)-9,11,15-trihydroxy-15-({2RS}-1,3-benzodioxan-2-yl)-16,17,18,19,20-pentanorprostenoic acid and the methyl ester thereof;

(13E)-(8R,9S,11R,15R)-9,11,15-trihydroxy-15-({2R}-1,3-benzodioxan-2-yl)-16,17,18,19,20-pentanorprostenoic acid and the methyl ester thereof;

(13E)-(8R,9S,11R,15S)-9,11,15-trihydroxy-15-({2R}-1,3-benzodioxan-2-yl)-16,17,18,19,20-pentanorprostenoic acid and the methyl ester thereof;

(13E)-(8R,9S,11R,15R)-9,11,15-trihydroxy-15-({2S}-1,3-benzodioxan-2-yl)-16,17,18,19,20-pentanorprostenoic acid and the methyl ester thereof;

(13E)-(8R,9S,11R,15S)-9,11,15-trihydroxy-15-({2S}-1,3-benzodioxan-2-yl)-16,17,18,19,20-pentanorprostenoic acid and the methyl ester thereof.

EXAMPLE 33

By interposing in the reaction sequence leading to the compounds of Examples 7–12 a reduction of compounds 7(d), 8(d), 9(d), 10(d), 11(d), 12(d) analogously to the process described for Example 31, then the following compounds are obtained:

(13E)-(8R,11R,12R,15R)-11,15-dihydroxy-9-oxo-15-({2RS}-1,3-benzodioxan-2-yl)-16,17,18,19,20-pentanorprostenoic acid and the methyl ester thereof;

(13E)-(8R,11R,12R,15S)-11,15-dihydroxy-9-oxo-15-({2RS}-1,3-benzodioxan-2-yl)-16,17,18,19,20-pentanorprostenoic acid and the methyl ester thereof;

(13E)-(8R,11R,12R,15R)-11,15-dihydroxy-9-oxo-15-({2R}-1,3-benzodioxan-2-yl)-16,17,18,19,20-pentanorprostenoic acid and the methyl ester thereof;

(13E)-(8R,11R,12R,15S)-11,15-dihydroxy-9-oxo-15-({2R}-1,3-benzodioxan-2-yl)-16,17,18,19,20-pentanorprostenoic acid and the methyl ester thereof;

(13E)-(8R,11R,12R,15R)-11,15-dihydroxy-9-oxo-15-({2S}-1,3-benzodioxan-2-yl)-16,17,18,19,20-pentanorprostenoic acid and the methyl ester thereof;

(13E)-(8R,11R,12R,15S)-11,15-dihydroxy-9-oxo-15-({2S}-1,3-benzodioxan-2-yl)-16,17,18,19,20-pentanorprostenoic acid and the methyl ester thereof.

EXAMPLE 34

(8R,9S,11R,12R,15R)-9,11,15-Trihydroxy-15-({2RS}-1,3-benzodioxan-2-yl)-16,17,18,19,20-pentanorprostanoic Acid and the Methyl Ester Thereof General Formula I: $A=B=CH_2-CH_2$;

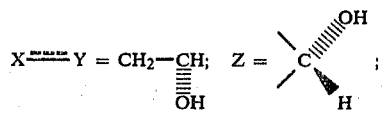

$R_1=OCH_3,OH$; $R_2$, $R_3$, $R_4=H$; the OH-group on the C-15 is in the α-position.

At room temperature and under a hydrogen atmosphere, 432 mg. of the ester or acid obtained according to Example 1, 45 mg. of palladium on charcoal (10%), and 10 ml. of ethyl acetate were shaken until 2 millimoles of hydrogen had been absorbed. Filtration and evaporation resulted in 420 mg. of the above compound as a colorless oil.

IR (Methyl ester): 3600-3400, 1730, 1590, 1490, 760 cm$^{-1}$.

EXAMPLE 35

Analogously to the process described in Example 34, the following derivatives were obtained with the compounds of Examples 2–6:

(8R,9S,11R,12R,15S)-9,11,15-trihydroxy-15-({2RS}-1,3-benzodioxan-2-yl)-16,17,18,19,20-pentanorprostanoic acid and the methyl ester thereof;

(8R,9S,11R,12R,15R)-9,11,15-trihydroxy-15-({2R}-1,3-benzodioxan-2-yl)-16,17,18,19,20-pentanorprostanoic acid and the methyl ester thereof;

(8R,9S,11R,12R,15S)-9,11,15-trihydroxy-15-({2R}-1,3-benzodioxan-2-yl)-16,17,18,19,20-pentanorprostanoic acid and the methyl ester thereof;

(8R,9S,11R,12R,15R)-9,11,15-trihydroxy-15-({2S}-1,3-benzodioxan-2-yl)-16,17,18,19,20-pentanorprostanoic acid and the methyl ester thereof;

(8R,9S,11R,12R,15S)-9,11,15-trihydroxy-15-({2S}-1,3-benzodioxan-2-yl)-16,17,18,19,20-pentanorprostanoic acid and the methyl ester thereof.

EXAMPLE 36

(5Z,13E)-(8R,9S,12R,15R)-9,15-Dihydroxy-11-oxo-15-({2R}-1,3-benzodioxan-2-yl)-16,17,18,19,20-pentanorprostadienoic Acid and the Methyl Ester Thereof General Formula I: A=trans—CH=CH; B=cis—CH=CH;

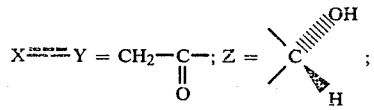

$R_1=OCH_3,OH$; $R_2$, $R_3$, $R_4=H$; the OH-group on C-15 is in the α-position.

(a)

(1S,5R,6R,7R,3′R)-6-[(E)-3-Tetrahydropyranyloxy-3-({2RS}-1,3-benzodioxan-2-yl)-1-propenyl]-7-benzoyloxy-2-oxabicyclo[3,3,0]octan-3-one At ice bath temperature, 3 ml. of freshly distilled dihydropyran and 10 mg. of p-toluenesulfonic acid were added to a solution of 2.4 g. of the α-alcohol obtained according to Example 1(d) in 50 ml. of methylene chloride; the mixture was agitated for 15 minutes at this temperature, diluted with methylene chloride, and shaken with sodium bicarbonate solution. The organic phase was washed with water, dried with magnesium sulfate, and evaporated under vacuum. Yield: 2.8 g. of the product.

(b)
(1S,5R,6R,7R,3'R)-6-[(E)-3-Tetrahydropyranyloxy-3-({2RS}-1,3-benzodioxan-2-yl)-1-propenyl]-7-hydroxy-2-oxabicyclo[3,3,0]octan-3-one A mixture of the 2.8 g. of product obtained according to (a) and 765 mg. of potassium carbonate (anhydrous) in 110 ml. of methanol (absolute) was stirred for 2 hours at room temperature under argon. The mixture was then diluted with ethyl acetate and washed with saturated sodium chloride solution so that the mixture became neutral. The organic phase was dried over magnesium sulfate and evaporated under vacuum, thus obtaining 1.85 g. of the title compound.

(c)
(2RS,3aR,4R,5R,6aS,3'R)-4-[(E)-3-Tetrahydropyranyloxy-3-({2RS}-1,3-benzodioxan-2-yl)-1-propenyl]-5-hydroxyperhydrocyclopenta[b]furan-2-ol Under argon, 22 ml. of a 20% DIBAH solution in toluene was added dropwise to a solution, cooled to −70° C., of 1.85 g. of the lactone obtained according to (b) in 90 ml. of absolute toluene. After 30 minutes, the reaction was terminated by the dropwise addition of isopropanol and agitated while adding 30 ml. of water for 15 minutes at 0° C. Thereafter, the mixture was extracted with ethyl acetate, washed with brine, dried with magnesium sulfate, and evaporated under vacuum. Yield: 1.8 g. of the title compound as a colorless oil.

(d)
(2RS,3aR,4R,5R,6aS,3'R)-4-[(E)-3-Tetrahydropyranyloxy-3-({2RS}-1,3-benzodioxan-2-yl)-1-propenyl]-2,5-diacetoxyperhydrocyclopenta[b]-furan-2-ol 1.8 g. of the lactol obtained according to (c) was agitated at room temperature in a mixture of 10 ml. of acetic anhydride and 25 ml. of pyridine for 8 hours. After the solvent had been removed under vacuum, 2.0 g. of the title compound was produced.

(e)
(2RS,3aR,4R,5R,6aS,3'R)-4-[(E)-3-Tetrahydropyranyloxy-3-({2RS}-1,3-benzodioxan-2-yl)-1-propenyl]-5-acetoxyperhydrocyclopenta[b]furan-2-ol 2.0 g. of the diacetate obtained according to (d) was maintained for 15 minutes at 25° C. in a mixture of 5 parts of glacial acetic acid, 5 parts of water, and one part of tetrahydrofuran. The mixture was then stirred into a sodium bicarbonate solution and washed neutral. The organic phase was concentrated, and the residue was purified by column chromatography on silica gel with ether/pentane=1:1. Yield: 1.5 g. of the title compound.

(f)
(5Z,13E)-(8R,9S,11R,12R,15R)-9-Hydroxy-11-acetoxy-15-tetrahydropyranyloxy-15-({2RS}-1,3-benzodioxan-2-yl)-16,17,18,19,20-pentanorprostadienoic Acid 26.3 ml. of a solution of methanesulfinylmethylsodium in absolute DMSO (solution: 2.5 g. of 50% sodium hydride suspension was stirred in 50 ml. of DMSO for 1 hour at 70° C.) was added dropwise to a solution of 7.2 g. of 4-carboxybutyltriphenylphosphonium bromide in 30 ml. of absolute dimethyl sulfoxide, and the mixture was stirred for 30 minutes at room temperature. This ylid solution was then added dropwise within 15 minutes to a solution of 1.5 g. of the lactol obtained according to (e) in 30 ml. of absolute DMSO; then, the mixture was agitated for 2 hours at 50° C. The solvent was thereafter extensively removed by distillation under an oil pump vacuum and at 45° C. The residue was taken up in 70 ml. of water and extracted three times with ether. The organic extract was discarded. The aqueous phase was acidified with 10% citric acid solution to pH 4–5 and extracted four times with a mixture of hexane/ether=1:1. The ether/hexane extract was washed with brine, dried over magnesium sulfate, and evaporated under vacuum. After chromatography of the residue on silica gel, 1.1 g. of the title compound was eluted as a colorless oil with ether.

(g)
(5Z,13E)-(8R,9S,11R,12R,15R)-9,15-Bis(tetrahydropyranyloxy)-11-acetoxy-15-({2RS}-1,3-benzodioxan-2-yl)-16,17,18,19,20-pentanorprostadienoic Acid A methylene chloride solution of 1.1 g. of the compound obtained according to (f) was combined at ice bath temperature with 2.2 ml. of dihydropyran and 6 mg. of p-toluenesulfonic acid and agitated for 15 minutes at this temperature. Subsequently the mixture was diluted with methylene chloride, extracted with sodium bicarbonate solution, the organic phase washed with water, dried over magnesium sulfate, and concentrated. The residue was treated for 15 minutes at 25° C. with a glacial acetic acid/water/THF mixture (5/5/1) and then introduced under agitation into a sodium bicarbonate solution and washed neutral. After the organic phase had been concentrated, 1.2 g. of a colorless oil was obtained as the product.

(h)
(5Z,13E)-(8R,9S,11R,12R,15R)-9,15-Bis(tetrahydropyranyloxy)-11-hydroxy-15-({2RS}-1,3-benzodioxan-2-yl)-16,17,18,19,20-pentanorprostadienoic Acid The 1.2 g. of product obtained according to (g) was reacted analogously to the directions given in (b) with potassium carbonate and methanol, thus obtaining 0.8 g. of the title compound.

(i)
(5Z,13E)-(8R,9S,12R,15R)-9,15-Bis(tetrahydropyranyloxy)-11-oxo-15-({2RS}-1,3-benzodioxan-2-yl)-16,17,18,19,20-pentanorprostadienoic Acid A solution of 0.8 g. of the alcohol obtained according to (h) in 10 ml. of acetone was mixed at −20° C. with 0.84 ml. of Jones reagent and then agitated for 30 minutes at −20° C. Thereafter, 1 ml. of isopropanol was added dropwise to the reaction mixture and the latter was stirred for 10 minutes at −20° C., then diluted with ether, and extracted three times with water. The organic phase was dried over magnesium sulfate and evaporated under vacuum, thus producing 725 mg. of the ketone as a colorless oil.

(j)
(5Z,13E)-(8R,9S,12R,15R)-9,15-Dihydroxy-11-oxo-15-({2RS}-1,3-benzodioxan-2-yl)-16,17,18,19,20-pentanorprostadienoic Acid 650 mg. of the bis(tetrahydropyranyl)ether produced according to (i) was agitated for 6 hours at 50° C. in 15 ml. of a mixture consisting of 65 parts of glacial acetic acid, 35 parts of water, and 10 parts of tetrahydrofuran. Thereafter, the mixture was evaporated to dryness at 0.1 torr, and the crude product was purified by column chromatography. With methylene chloride/5–8% ethanol 280 mg. of the title compound was eluted.

(k) At ice bath temperature, 7 ml. of an ethereal diazomethane solution was added dropwise to a solution of 140 mg. of the acid obtained according to (j) in 10 ml. of methylene chloride. The mixture was agitated for 10 minutes and then evaporated under vacuum. Chromatography of the crude product on silica gel with ether/dioxane=95/5 as the eluent yielded 80 mg. of the prostaglandin-carboxylic acid methyl ester of the D-type indicated as Example 36.

IR: 3500–3300, 1740, 1730, 1590, 1485, 980, 760 cm$^{-1}$.

EXAMPLE 37

Analogously to the process described in Example 36, the following derivatives were produced, starting with the compounds of Examples 2(a), 3(b), 4(a), 5(b), and 6(a):

(5Z,13E)-(8R,9S,12R,15S)-9,15-dihydroxy-11-oxo-15-({2RS}-1,3-benzodioxan-2-yl)-16,17,18,19,20-pentanorprostadienoic acid and the methyl ester thereof;

(5Z,13E)-(8R,9S,12R,15R)-9,15-dihydroxy-11-oxo-15-({2R}-1,3-benzodioxan-2-yl)-16,17,18,19,20-pentanorprostadienoic acid and the methyl ester thereof;

(5Z,13E)-(8R,9S,12R,15S)-9,15-dihydroxy-11-oxo-15-({2R}-1,3-benzodioxan-2-yl)-16,17,18,19,20-pentanorprostadienoic acid and the methyl ester thereof;

(5Z,13E)-(8R,9S,12R,15R)-9,15-dihydroxy-11-oxo-15-({2S}-1,3-benzodioxan-2-yl)-16,17,18,19,20-pentanorprostadienoic acid and the methyl ester thereof;

(5Z,13E)-(8R,9S,12R,15S)-9,15-dihydroxy-11-oxo-15-({2S}-1,3-benzodioxan-2-yl)-16,17,18,19,20-pentanorprostadienoic acid and the methyl ester thereof.

EXAMPLE 38

(5Z,13E)-(8R,9S,11R,12R,15R)-9,11,15-Trihydroxy-15-({2RS}-1,3-benzodioxane-6-brom-2-yl)-16,17,18,19,20-pentanorprostadienoic Acid and the Methyl Ester Thereof General Formula I: A=trans—CH=CH; B=cis—CH=CH;

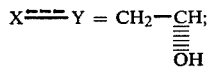

$R_1$=OCH$_3$,OH: $R_2$, $R_4$=H; $R_3$=Br (in the p-position with respect to the phenolic oxygen); the OH-group on C-15 is in the α-position.

(a) 5-Bromo-2-hydroxybenzyl Alcohol

At 0°–5° C., 11.5 ml. of bromine in 100 ml. of carbon tetrachloride was added dropwise to a suspension of 24.8 g. of saligenin and 24 g. of calcium carbonate in a solvent mixture of 200 ml. of carbon tetrachloride and 220 ml. of methylene chloride. The reaction mixture was stirred for 24 hours at room temperature, then filtered, and the precipitate was washed with carbon tetrachloride. The CCl$_4$/CH$_2$Cl$_2$ phase was discarded. The solid substance was taken up in ethyl acetate/water, and the organic phase was separated, dried over magnesium sulfate, and evaporated to dryness. The residue was recrystallized from methylene chloride, thus obtaining colorless crystal flakes (24 g.). Melting point: 107°–109° C. (methylene chloride).

(b) 1,3-Benzodioxane-6-bromo-2-carboxylic Acid Methyl Ester

Under ice water cooling, a solution of 20.3 g. of the 5-bromo-2-hydroxybenzyl alcohol obtained according to (a) in 110 ml. of dimethylformamide was added dropwise to a suspension of 9.6 g. of 50% sodium hydride in 100 ml. of dimethylformamide. The reaction mixture was stirred overnight at room temperature. Thereafter, 8.62 ml. of dichloroacetic acid was added dropwise under ice cooling in 100 ml. of dimethylformamide. Under further ice cooling, 5.04 g. of 50% sodium hydride was then added to the reaction mixture in incremental portions. This sodium dichloroacetate solution was agitated for 30 minutes at room temperature and then introduced dropwise into the first-prepared bromosaligenin disodium solution. After the addition of 1.5 g. of sodium iodide, the reaction mixture was agitated for 4.5 hours at 60° C.; during the last 2.5 hours, the largest part of the dimethylformamide was distilled off under vacuum during this procedure. After cooling, the residue was acidified to pH 3 with aqueous citric acid solution, then saturated with sodium chloride, and extracted repeatedly with methylene chloride. The organic phase was dried over magnesium sulfate, concentrated with the aid of a forced-circulation evaporator, and combined at 0° C. with ethereal diazomethane solution until there was no longer any evolution of gas, and the reaction solution assumed permanently a yellow coloring. The solvent was removed after stirring for one-half hour at room temperature under vacuum, together with excess diazomethane. The remaining, light-colored crystalline slurry was purified by column chromatography on silica gel with methylene chloride or hexane/10% ethyl acetate as the eluent.

Yield: 12.6 g., m.p. 120° C. (matted, small needles of methylene chloride/hexane).

(c)
[2-Oxo-2-(1,3-benzodioxane-6-brom-2-yl)-ethylidene]-triphenylphosphorane

Under ice cooling and under an argon atmosphere, 15.63 ml. of a 2.15-molar butyllithium solution in hexane was added dropwise to a suspension of 13 g. of triphenylmethylphosphonium bromide (4 hours of drying at 40° C. with the use of an oil pump) in 85 ml. of absolute ether. The mixture was then agitated for 15 hours at room temperature. The yellow ylene solution was combined dropwise with 4.59 g. of the 1,3-benzodioxane-6-bromo-2-carboxylic acid methyl ester obtained according to (b) in 75 ml. of absolute benzene, and the mixture was stirred for 1 hour at room temperature. The white precipitate was filtered off, dissolved in water, and extracted with ether. The organic phase was combined with the filtrate, washed with water, dried over magnesium sulfate, and concentrated to dryness. The residue was purified by column chromatography on silica gel with hexane/20–100% ethyl acetate. Yield: 5.6 g.

Melting point: 172°–174° C. (ethyl acetate).

The further reaction steps were conducted analogously to the directions in 1(c)–(g).

Analogously, all other prostaglandin acids and esters described in the present examples can also be converted into the derivatives corresponding to Example 38.

EXAMPLE 39

(5Z,13E)-(8R,9S,11R,12R,15R)-9,11,15-Trihydroxy-15-({2RS}-1,3-benzodioxan-2-yl)-16,17,18,19,20-pentanor-prostadienoic Acid (4-Phenyl)-phenacyl Ester General Formula I: A=trans—CH=CH; B=cis—CH=CH;

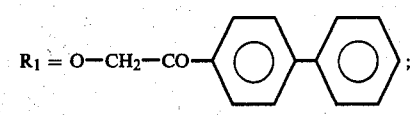

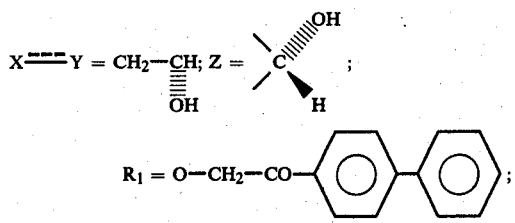

$R_2$, $R_3$, $R_4$=H; the OH-group on C-15 is in the α-position.

At room temperature, 75 mg. of the prostadienoic acid obtained according to Example 1(f) was agitated with 21 mg. of triethylamine and 53 mg. of p-phenylphenacyl bromide in 4 ml. of acetone for 12 hours under an argon atmosphere. After dilution with water, the reaction mixture was extracted with ether, the ether extract shaken with NaCl solution, dried over magnesium sulfate, and evaporated under vacuum. The residue was filtered over 5 g. of silica gel with ether/dioxan mixtures. Recrystallization from methylene chloride/hexane yielded 55 mg. of the title compound in the form of colorless crystals.

Melting point: 118° C.

IR: 3600, 1740, 1695, 1590, 1490, 980, 750 cm$^{-1}$.

In analogy to Example 39, all other prostaglandin acids described in the above examples can be likewise converted to the corresponding phenacyl esters.

EXAMPLE 40

Tris(hydroxymethyl)aminomethane Salt of (5Z,13E)-(8R,9S,11R,12R,15R)-9,11,15-Trihydroxy-15-({2RS}-1,3-benzodioxan-2-yl)-16,17,18,19,20-pentanor-prostadienoic Acid At 60° C., a solution of 32.9 mg. of tris(hydroxymethyl)aminomethane in 0.1 ml. of water was added to a solution of 103 mg. of the prostadienoic acid produced according to Example 1(f) in 14 ml. of acetonitrile. The mixture was allowed to stand at room temperature for 14 hours, thus obtaining 76 mg. of the above salt as colorless crystals.

Analogously to Example 40, all other prostaglandin acids described in the above examples can likewise be converted into the corresponding tris(hydroxymethyl)aminomethane salts.

EXAMPLE 41

(5Z,13E)-(8R,9S,11R,12R,15R)-9,11,15-Trihydroxy-15-({2S}-1,3-benzodioxan-2-yl)-16,17,18,19,20-pentanor-prostadienoic Acid (4-Phenyl)-phenacyl Ester General Formula I: A=trans—CH=CH; B=cis—CH=CH;

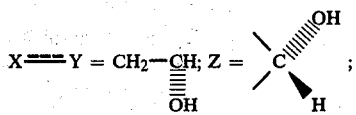

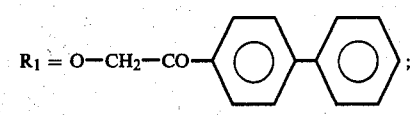

$R_2$, $R_3$, $R_4$=H; the OH-group on C-15 is in the α-position.

130 mg. of the prostadienoic acid obtained according to Example 5(d) were reacted analogously to Example 39, thus obtaining 85 mg. of the title compound as colorless crystals.

Melting point: 79° C.–80° C.

IR: 3430, 1745, 1695, 1585, 1225, 1030, 760, 750, 720 cm$^{-1}$.

EXAMPLE 42

(5Z,13E)-(8R,9S,11R,12R,15S)-9,11,15-Trihydroxy-15-({2S}-1,3-benzodioxan-2-yl)-16,17,18,19,20-pentanor-prostadienoic Acid (4-Phenyl)-phenacyl Ester General Formula I: A=trans—CH=CH; B=cis—CH=CH;

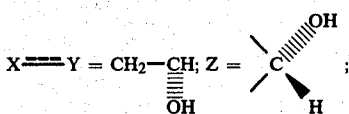

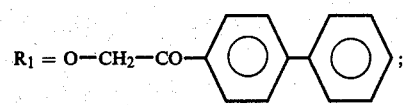

$R_2$, $R_3$, $R_4$=H; the OH-group on C-15 is in the β-position.

100 mg. of the prostadienoic acid obtained according to Example 6(c) was reacted analogously to Example 39, thus producing 115 mg. of the title compound in the form of colorless crystals; m.p. 60° C.

IR: 3440, 1740, 1700, 1590, 1240, 1030, 760, 725 cm$^{-1}$.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1,3-benzodioxaneprostanoic acid compound of the formula

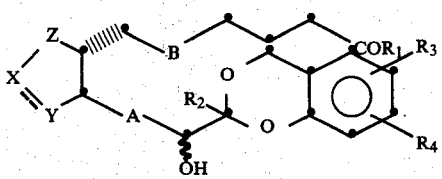

wherein $R_1$ is (a) hydroxy, (b) alkoxy of 1–10 carbon atoms, (c) methylsulfamido, (d) phenoxy, (e) 1- or 2-naphthoxy, (f) phenoxy or 1- or 2-naphthoxy substituted by 1–3 halogen atoms, phenyl, phenoxy, 1–3 alkyl or alkoxy groups of 1–4 carbon atoms each or one each of chloromethyl, fluoromethyl, trifluoromethyl, carboxy or hydroxy or (g) O—CH$_2$—U—V, wherein U is a direct bond, carbonyl or carbonyloxy, and V is phenyl or phenyl substituted by one or more of phenyl, phenoxy, alkoxy of 1–2 carbon atoms or halogen;

A is —CH$_2$—CH$_2$ or trans—CH=CH—;
B is —CH$_2$—CH$_2$— or cis- or trans—CH=CH—;
Z is hydroxymethylene or carbonyl;
X ≡≡≡≡Y, if Z is hydroxymethylene, is

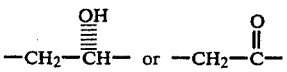

or, if Z is carbonyl, is

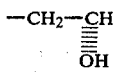

or —CH=CH—;
$R_2$ is hydrogen or alkyl of 1–5 carbon atoms;
$R_3$ and $R_4$ each are H, F, Cl, Br, I, CF$_3$, CH$_3$, or alkoxy of 1–2 carbon atoms or $R_3$ and $R_4$ in 6-, 7-position is methylenedioxy; and, when $R_1$ is hydroxy, salts thereof with pharmaceutically acceptable bases.

2. A compound of claim 1, wherein A is —CH$_2$CH$_2$—.
3. A compound of claim 1, wherein A is trans-—CH=CH—.
4. A compound of claim 1, wherein B is —CH$_2$CH$_2$—.
5. A compound of claim 1, wherein B is cis- —CH=CH—.
6. A compound of claim 1, wherein B is trans-—CH=CH—.
7. A compound of claim 1, wherein Z is hydroxymethylene and X≡≡≡≡Y is

8. A compound of claim 1, wherein Z is hydroxymethylene and X≡≡≡≡Y is

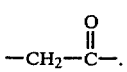

9. A compound of claim 1, wherein Z is carbonyl and X≡≡≡≡Y is

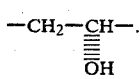

10. A compound of claim 1, wherein Z is carbonyl and X≡≡≡≡Y is —CH=CH—.
11. A compound of claim 1, wherein $R_1$ is hydroxy.
12. A compound of claim 1, wherein $R_1$ is alkoxy of 1–10 carbon atoms.

13. A compound of claim 1, wherein $R_1$ is methoxy and $R_3$ and $R_4$ are H.
14. A compound of claim 1, wherein $R_1$ is p-phenylphenacyloxy and $R_3$ and $R_4$ are H.
15. (5Z,13E)-(8R,9S,11R,12R,15R)-9,11,15-Trihydroxy-15-({2RS}-1,3-benzodioxan-2-yl)-16,17,18,19,20-pentanorprostadienoic acid, a compound of claim 1.
16. (5Z,13E)-(8R,9S,11R,12R,15S)-9,11,15-Trihydroxy-15-({2RS}-1,3-benzodioxan-2-yl)-16,17,18,19,20-pentanorprostadienoic acid, a compound of claim 1.
17. (5Z,13E)-(8R,9S,11R,12R,15R)-9,11,15-Trihydroxy-15-({2R}-1,3-benzodioxan-2-yl)-16,17,18,19,20-pentanorprostadienoic acid, a compound of claim 1.
18. (5Z,13E)-(8R,9S,11R,12R,15S)-9,11,15-Trihydroxy-15-({2R}-1,3-benzodioxan-2-yl)-16,17,18,19,20-pentanorprostadienoic acid, a compound of claim 1.
19. (5Z,13E)-(8R,9S,11R,12R,15R)-9,11,15-Trihydroxy-15-({2S}-1,3-benzodioxan-2-yl)-16,17,18,19,20-pentanorprostadienoic acid, a compound of claim 1.
20. (5Z,13E)-(8R,9S,11R,12R,15S)-9,11,15-Trihydroxy-15-({2S}-1,3-benzodioxan-2-yl)-16,17,18,19,20-pentanorprostadienoic acid, a compound of claim 1.
21. (5Z,13E)-(8R,11R,12R,15R)-11,15-Dihydroxy-9-oxo-15-({2RS}-1,3-benzodioxan-2-yl)-16,17,18,19,20-pentanorprostadienoic acid, a compound of claim 1.
22. (5Z,13E)-(8R,11R,12R,15S)-11,15-Dihydroxy-9-oxo-15-({2RS}-1,3-benzodioxan-2-yl)-16,17,18,19,20-pentanorprostadienoic acid, a compound of claim 1.
23. (5Z,13E)-(8R,11R,12R,15R)-11,15-Dihydroxy-9-oxo-15-({2R}-1,3-benzodioxan-2-yl)-16,17,18,19,20-pentanorprostadienoic acid, a compound of claim 1.
24. (5Z,13E)-(8R,11R,12R,15S)-11,15-Dihydroxy-9-oxo-15-({2R}-1,3-benzodioxan-2-yl)-16,17,18,19,20-pentanorprostadienoic acid, a compound of claim 1.
25. (5Z,13E)-(8R,11R,12R,15R)-11,15-Dihydroxy-9-oxo-15-({2S}-1,3-benzodioxan-2-yl)-16,17,18,19,20-pentanorprostadienoic acid, a compound of claim 1.
26. (5Z,13E)-(8R,11R,12R,15S)-11,15-Dihydroxy-9-oxo-15-({2S}-1,3-benzodioxan-2-yl)-16,17,18,19,20-pentanorprostadienoic acid, a compound of claim 1.
27. (5Z)-(8R,9S,11R,12R,15R)-9,11,15-Trihydroxy-15-({2RS}-1,3-benzodioxan-2-yl)-16,17,18,19,20-pentanorprostenoic acid, a compound of claim 1.
28. (5Z)-(8R,9S,11R,12R,15S)-9,11,15-Trihydroxy-15-({2RS}-1,3-benzodioxan-2-yl)-16,17,18,19,20-pentanorprostenoic acid, a compound of claim 1.
29. (5Z)-(8R,9S,11R,12R,15R)-9,11,15-Trihydroxy-15-({2R}-1,3-benzodioxan-2-yl)-16,17,18,19,20-pentanorprostenoic acid, a compound of claim 1.
30. (5Z)-(8R,9S,11R,12R,15S)-9,11,15-Trihydroxy-15-({2R}-1,3-benzodioxan-2-yl)-16,17,18,19,20-pentanorprostenoic acid, a compound of claim 1.
31. (5Z)-(8R,9S,11R,12R,15R)-9,11,15-Trihydroxy-15-({2S}-1,3-benzodioxan-2-yl)-16,17,18,19,20-pentanorprostenoic acid, a compound of claim 1.
32. (5Z)-(8R,9S,11R,12R,15S)-9,11,15-Trihydroxy-15-({2S}-1,3-benzodioxan-2-yl)-16,17,18,19,20-pentanorprostenoic acid, a compound of claim 1.
33. (5Z)-(8R,11R,12R,15R)-11,15-Dihydroxy-9-oxo-15-({2RS}-1,3-benzodioxan-2-yl)-16,17,18,19,20-pentanorprostenoic acid, a compound of claim 1.
34. (5Z)-(8R,11R,12R,15S)-11,15-Dihydroxy-9-oxo-15-({2RS}-1,3-benzodioxan-2-yl)-16,17,18,19,20-pentanorprostenoic acid, a compound of claim 1.
35. (5Z)-(8R,11R,12R,15R)-11,15-Dihydroxy-9-oxo-15-({2R}-1,3-benzodioxan-2-yl)-16,17,18,19,20-pentanorprostenoic acid, a compound of claim 1.

36. (5Z)-(8R,11R,12R,15S)-11,15-Dihydroxy-9-oxo-15-({2R}-1,3-benzodioxan-2-yl)-16,17,18,19,20-pentanorprostenoic acid, a compound of claim 1.

37. (5Z)-(8R,11R,12R,15R)-11,15-Dihydroxy-9-oxo-15-({2S}-1,3-benzodioxan-2-yl)-16,17,18,19,20-pentanorprostenoic acid, a compound of claim 1.

38. (5Z)-8R,11R,12R,15S)-11,15-Dihydroxy-9-oxo-15-({2S}-1,3-benzodioxan-2-yl)-16,17,18,19,20-pentanorprostenoic acid, a compound of claim 1.

39. (5Z,10Z,13E)-(8R,12S,15R)-15-Hydroxy-9-oxo-15-({2RS}-1,3-benzodioxan-2-yl)-16,17,18,19,20-pentanorprostatrienoic acid, a compound of claim 1.

40. (5Z,10Z,13E)-(8R,12S,15S)-15-Hydroxy-9-oxo-15-({2RS}-1,3-benzodioxan-2-yl)-16,17,18,19,20-pentanorprostatrienoic acid, a compound of claim 1.

41. (5Z,10Z,13E)-(8R,12S,15R)-15-Hydroxy-9-oxo-15-({2R}-1,3-benzodioxan-2-yl)-16,17,18,19,20-pentanorprostatrienoic acid, a compound of claim 1.

42. (5Z,10Z,13E)-(8R,12S,15S)-15-Hydroxy-9-oxo-15-({2R}-1,3-benzodioxan-2-yl)-16,17,18,19,20-pentanorprostatrienoic acid, a compound of claim 1.

43. (5Z,10Z,13E)-(8R,12S,15R)-15-Hydroxy-9-oxo-15-({2S}-1,3-benzodioxan-2-yl)-16,17,18,19,20-pentanorprostatrienoic acid, a compound of claim 1.

44. (5Z,10Z,13E)-(8R,12S,15S)-15-Hydroxy-9-oxo-15-({2S}-1,3-benzodioxan-2-yl)-16,17,18,19,20-pentanorprostatrienoic acid, a compound of claim 1.

45. (13E)-(8R,9S,11R,12R,15R)-9,11,15-Trihydroxy-15-({2RS}-1,3-benzodioxan-2-yl)-16,17,18,19,20-pentanorprostenoic acid, a compound of claim 1.

46. (13E)-(8R,9S,11R,12R,15S)-9,11,15-Trihydroxy-15-({2RS}-1,3-benzodioxan-2-yl)-16,17,18,19,20-pentanorprostenoic acid, a compound of claim 1.

47. (13E)-(8R,9S,11R,15R-9,11,15-Trihydroxy-15-({2R}-1,3-benzodioxan-2-yl)-16,17,18,19,20-pentanorprostenoic acid, a compound of claim 1.

48. (13E)-(8R,9S,11R,15S)-9,11,15-Trihydroxy-15-({2R}-1,3-benzodioxan-2-yl)-16,17,18,19,20-pentanorprostenoic acid, a compound of claim 1.

49. (13E)-(8R,9S,11R,15R)-9,11,15-Trihydroxy-15-({2S}-1,3-benzodioxan-2-yl)-16,17,18,19,20-pentanorprostenoic acid, a compound of claim 1.

50. (13E)-(8R,9S,11R,15S)-9,11,15-Trihydroxy-15-({2S}-1,3-benzodioxan-2-yl)-16,17,18,19,20-pentanorprostenoic acid, a compound of claim 1.

51. (13E)-(8R,11R,12R,15R)-11,15-Dihydroxy-9-oxo-15-({2RS}-1,3-benzodioxan-2-yl)-16,17,18,19,20-pentanorprostenoic acid, a compound of claim 1.

52. (13E)-(8R,11R,12R,15S)-11,15-Dihydroxy-9-oxo-15-({2RS}-1,3-benzodioxan-2-yl)-16,17,18,19,20-pentanorprostenoic acid, a compound of claim 1.

53. (13E)-(8R,11R,12R,15R)-11,15-Dihydroxy-9-oxo-15-({2R}-1,3-benzodioxan-2-yl)-16,17,18,19,20-pentanorprostenoic acid, a compound of claim 1.

54. (13E)-(8R,11R,12R,15S)-11,15-Dihydroxy-9-oxo-15-({2R}-1,3-benzodioxan-2yl)-16,17,18,19,20-pentanorprostenoic acid, a compound of claim 1.

55. (13E)-(8R,11R,12R,15R)-11,15-Dihydroxy-9-oxo-15-({2S}-1,3-benzodioxan-2-yl)-16,17,18,19,20-pentanorprostenoic acid, a compound of claim 1.

56. (13E)-(8R,11R,12R,15S)-11,15-Dihydroxy-9-oxo-15-({2S}-1,3-benzodioxan-2-yl)-16,17,18,19,20-pentanorprostenoic acid, a compound of claim 1.

57. (8R,9S,11R,12R,15R)-9,11,15-Trihydroxy-15-({2RS}-1,3-benzodioxan-2-yl)-16,17,18,19,20-pentanorprostanoic acid, a compound of claim 1.

58. (8R,9S,11R,12R,15S)-9,11,15-Trihydroxy-15-({2RS}-1,3-benzodioxan-2-yl)-16,17,18,19,20-pentanorprostanoic acid, a compound of claim 1.

59. (8R,9S,11R,12R,15R)-9,11,15-Trihydroxy-15-({2R}-1,3-benzodioxan-2-yl)-16,17,18,19,20-pentanorprostanoic acid, a compound of claim 1.

60. (8R,9S,11R,12R,15S)-9,11,15-Trihydroxy-15-({2R}-1,3-benzodioxan-2-yl)-16,17,18,19,20-pentanorprostanoic acid, a compound of claim 1.

61. (8R,9S,11R,12R,15R)-9,11,15-Trihydroxy-15-({2S}-1,3-benzodioxan-2-yl)-16,17,18,19,20-pentanorprostanoic acid, a compound of claim 1.

62. (8R,9S,11R,12R,15S)-9,11,15-Trihydroxy-15-({2S}-1,3-benzodioxan-2-yl)-16,17,18,19,20-pentanorprostanoic acid, a compound of claim 1.

63. (5Z,13E)-(8R,9S,12R,15R)-9,15-Dihydroxy-11-oxo-15-({2RS}-1,3-benzodioxan-2-yl)-16,17,18,19,20-pentanorprostadienoic acid, a compound of claim 1.

64. (5Z,13E)-(8R,9S,12R,15S)-9,15-Dihydroxy-11-oxo-15-({2RS}-1,3-benzodioxan-2-yl)-16,17,18,19,20-pentanorprostadienoic acid, a compound of claim 1.

65. (5Z,13E)-(8R,9S,12R,15R)-9,15-Dihydroxy-11-oxo-15-({2R}-1,3-benzodioxan-2-yl)-16,17,18,19,20-pentanorprostadienoic acid, a compound of claim 1.

66. (5Z,13E)-(8R,9S,12R,15S)-9,15-Dihydroxy-11-oxo-15-({2R}-1,3-benzodioxan-2-yl)-16,17,18,19,20-pentanorprostadienoic acid, a compound of claim 1.

67. (5Z,13E)-(8R,9S,12R,15R)-9,15-Dihydroxy-11-oxo-15-({2S}-1,3-benzodioxan-2-yl)-16,17,18,19,20-pentanorprostadienoic acid, a compound of claim 1.

68. (5Z,13E)-(8R,9S,12R,15S)-9,15-Dihydroxy-11-oxo-15-({2S}-1,3-benzodioxan-2-yl)-16,17,18,19,20-pentanorprostadienoic acid, a compound of claim 1.

69. (5Z,13E)-(8R,9S,11R,12R,15R)-9,11,15-Trihydroxy-15-({2RS}-1,3-benzodioxane-6-brom-2-yl)-16,17,18,19,20-pentanorprostadienoic acid, a compound of claim 1.

70. (5Z,13E)-(8R,9S,11R,12R,15R)-9,11,15-Trihydroxy-15-({2RS}-1,3-benzodioxan-2-yl)-16,17,18,19,20-pentanorprostadienoic acid (4-phenyl)-phenacyl ester, a compound of claim 1.

71. Tris(hydroxymethyl)-aminomethane salt of (5Z,13E)-(8R,9S,11R,12R,15R)-9,11,15-trihydroxy-15-({2RS}-1,3-benzodioxan-2-yl)-16,17,18,19,20-pentanorprostadienoic acid, a compound of claim 1.

72. (4-Phenyl)-phenacyl ester of (5Z,13E)-(8R,9S,11R,12R,15R)-9,11,15-trihydroxy-15-({2S}-1,3-benzodioxan-2-yl)-16,17,18,19,20-pentanorprostadienioc acid, a compound of claim 1.

73. (4-Phenyl)-phenacyl ester of (5Z,13E)-(8R,9S,11R,12R,15S)-9,11,15-trihydroxy-15-({2S}-1,3-benzodioxan-2-yl)-16,17,18,19,20-pentanorprostadienoic acid, a compound of claim 1.

74. A lactol of the formula

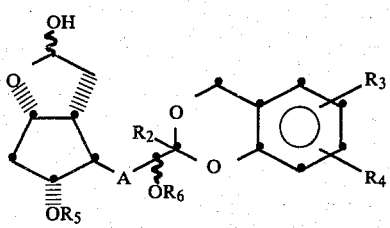

wherein $R_2$ is H or alkyl of 1–5 carbon atoms;

$R_3$ and $R_4$ each are H, F, Cl, Br, I, $CF_3$ $CH_3$ or alkoxy of 1-2 carbon atoms or $R_3$ and $R_4$ in 6-, 7-position is methylendioxy;

$R_5O-$ and $R_6O-$ are Oh, acyloxy wherein acyl is the acyl radical of an organic carboxylic acid, or a readily cleavable ether group; and A is $-CH_2CH_2-$ or trans- $-CH=CH-$.

75. A pharmaceutical composition comprising a lutrohytically effective amount of a compound of claim 1, in admixture with a pharmaceutically acceptable carrier.

76. A method of achieving a luteolytic effect in a patient which comprises administering to the patient a luteolytically effective amount of a compound of claim 1.

* * * * *